(12) United States Patent
Dholakia et al.

(10) Patent No.: US 12,070,220 B2
(45) Date of Patent: Aug. 27, 2024

(54) DEVICES HAVING MULTIPLE PERMEABLE SHELLS FOR TREATMENT OF VASCULAR DEFECTS

(71) Applicant: MICROVENTION, INC., Aliso Viejo, CA (US)

(72) Inventors: Ronak Dholakia, Los Angeles, CA (US); Hussain S. Rangwala, Villa Park, CA (US); William R. Patterson, Huntington Beach, CA (US)

(73) Assignee: MICROVENTION, INC., Aliso Viejo, CA (US)

( * ) Notice: Subject to any disclaimer, the term of this patent is extended or adjusted under 35 U.S.C. 154(b) by 23 days.

(21) Appl. No.: 17/197,975

(22) Filed: Mar. 10, 2021

(65) Prior Publication Data

US 2021/0282785 A1   Sep. 16, 2021

Related U.S. Application Data

(60) Provisional application No. 62/988,076, filed on Mar. 11, 2020.

(51) Int. Cl.
*A61B 17/12* (2006.01)

(52) U.S. Cl.
CPC .. *A61B 17/12113* (2013.01); *A61B 17/12145* (2013.01); *A61B 17/12172* (2013.01); *A61B 2017/1205* (2013.01)

(58) Field of Classification Search
CPC ........ A61B 17/12113; A61B 17/12145; A61B 17/12172; A61B 2017/1205; A61B 17/1214; A61B 17/1215; A61B 17/12154; A61B 2017/00898; A61B 2017/12095; A61B 17/12163
See application file for complete search history.

(56) References Cited

U.S. PATENT DOCUMENTS

| | | |
|---|---|---|
| 3,874,388 A | 4/1975 | King et al. |
| 4,282,875 A | 8/1981 | Serbinenko |
| 4,346,712 A | 8/1982 | Handa et al. |
| 4,402,319 A | 9/1983 | Handa et al. |
| 4,619,246 A | 10/1986 | Molgaard-Nielsen et al. |
| 4,675,361 A | 6/1987 | Ward |
| 4,729,278 A | 3/1988 | Graeff |

(Continued)

FOREIGN PATENT DOCUMENTS

| | | |
|---|---|---|
| AU | 2009242528 | 3/2016 |
| CA | 2722037 | 10/2009 |

(Continued)

OTHER PUBLICATIONS

A Complete Microcatheter Portfolio; A Broad Selection of Microcatheters. Boston Scientific Brochure 2007, pp. 1-2.

(Continued)

*Primary Examiner* — Ariana Zimbouski
*Assistant Examiner* — Mikail A Mannan
(74) *Attorney, Agent, or Firm* — ONE LLP

(57) ABSTRACT

Devices and methods for treatment of a patient's vasculature are described. Embodiments may include a device that includes a plurality of permeable shells connected by a plurality of coils, each coil connecting at least one pair of permeable shells. The plurality of coils may include an inert hydrogel core that absorbs water.

22 Claims, 17 Drawing Sheets

(56) References Cited

U.S. PATENT DOCUMENTS

| | | |
|---|---|---|
| 4,998,539 A | 3/1991 | Delsanti |
| 5,061,275 A | 10/1991 | Wallsten et al. |
| 5,071,407 A | 12/1991 | Termin et al. |
| 5,108,407 A | 4/1992 | Geremia et al. |
| 5,122,136 A | 6/1992 | Gluglielmi et al. |
| 5,154,705 A | 10/1992 | Fleischhacker et al. |
| 5,158,545 A | 10/1992 | Trudell et al. |
| 5,165,421 A | 11/1992 | Fleischhacker et al. |
| 5,263,963 A | 11/1993 | Garrison |
| 5,334,210 A | 8/1994 | Gianturco |
| 5,378,239 A | 1/1995 | Termin |
| 5,536,247 A | 7/1996 | Thornton |
| 5,562,725 A | 10/1996 | Schmitt et al. |
| 5,569,245 A | 10/1996 | Gluglielmi et al. |
| 5,578,074 A | 11/1996 | Mirigian |
| 5,591,222 A | 1/1997 | Susawa et al. |
| 5,601,595 A | 2/1997 | Smith |
| 5,630,840 A | 5/1997 | Mayer |
| D380,266 S | 6/1997 | Boatman et al. |
| 5,645,559 A | 7/1997 | Hachtman et al. |
| 5,725,552 A | 3/1998 | Kotula |
| 5,725,570 A | 3/1998 | Heath |
| 5,733,294 A | 3/1998 | Forber |
| 5,749,883 A | 5/1998 | Halpern |
| 5,759,161 A | 6/1998 | Ogawa |
| 5,766,219 A | 6/1998 | Horton |
| 5,846,261 A | 12/1998 | Kotula et al. |
| 5,873,907 A | 2/1999 | Frantzen |
| 5,907,893 A | 6/1999 | Zadno-Azizi |
| 5,916,235 A | 6/1999 | Guglielmi |
| 5,925,060 A | 7/1999 | Forber |
| 5,927,345 A | 7/1999 | Samson |
| 5,928,260 A | 7/1999 | Chin et al. |
| 5,935,148 A | 8/1999 | Villar et al. |
| 5,944,733 A | 8/1999 | Engelson |
| 5,944,738 A | 8/1999 | Amplatz |
| 5,951,599 A | 9/1999 | McCrory |
| 5,964,797 A | 10/1999 | Ho |
| 5,980,554 A | 11/1999 | Lenker et al. |
| 5,984,929 A | 11/1999 | Bashiri et al. |
| 5,989,242 A | 11/1999 | Saadat et al. |
| 6,033,423 A | 3/2000 | Ken et al. |
| 6,063,070 A | 5/2000 | Eder |
| 6,063,104 A | 5/2000 | Villar et al. |
| 6,086,577 A | 7/2000 | Ken et al. |
| 6,093,199 A | 7/2000 | Brown et al. |
| 6,123,715 A | 9/2000 | Amplatz |
| 6,139,564 A | 10/2000 | Teoh et al. |
| 6,142,975 A | 11/2000 | Jalisi et al. |
| 6,152,144 A | 11/2000 | Lesh et al. |
| 6,156,061 A | 12/2000 | Wallace et al. |
| 6,159,206 A | 12/2000 | Ogawa |
| 6,168,615 B1 | 1/2001 | Ken et al. |
| 6,168,618 B1 | 1/2001 | Frantzen |
| 6,168,622 B1 | 1/2001 | Mazzocchi |
| 6,190,402 B1 | 2/2001 | Horton et al. |
| 6,193,708 B1 | 2/2001 | Ken et al. |
| 6,203,779 B1 | 3/2001 | Ricci et al. |
| 6,221,086 B1 | 4/2001 | Forber |
| 6,238,403 B1 | 5/2001 | Greene, Jr. et al. |
| 6,277,126 B1 | 8/2001 | Barry et al. |
| 6,290,721 B1 | 9/2001 | Heath |
| 6,315,709 B1 | 11/2001 | Garibaldi et al. |
| 6,325,815 B1 | 12/2001 | Kusleika |
| 6,342,068 B1 | 1/2002 | Thompson |
| 6,344,048 B1 | 2/2002 | Chin et al. |
| 6,346,117 B1 | 2/2002 | Greenhalgh |
| 6,350,270 B1 | 2/2002 | Roue |
| 6,368,338 B1 | 4/2002 | Konya |
| 6,368,339 B1 | 4/2002 | Amplatz |
| 6,375,668 B1 | 4/2002 | Gifford |
| 6,375,670 B1 | 4/2002 | Greenhalgh |
| 6,383,174 B1 | 5/2002 | Eder |
| 6,391,037 B1 | 5/2002 | Greenhalgh |
| 6,425,914 B1 | 7/2002 | Wallace et al. |
| 6,428,558 B1 | 8/2002 | Jones et al. |
| 6,447,531 B1 | 9/2002 | Amplatz |
| 6,454,780 B1 | 9/2002 | Wallace |
| 6,461,370 B1 | 10/2002 | Gray et al. |
| 6,463,317 B1 | 10/2002 | Kucharczyk |
| 6,468,266 B1 | 10/2002 | Bashiri et al. |
| 6,478,773 B1 | 11/2002 | Gandhi et al. |
| 6,500,149 B2 | 12/2002 | Gandhi et al. |
| 6,506,204 B2 | 1/2003 | Mazzocchi |
| 6,511,468 B1 | 1/2003 | Cragg et al. |
| 6,551,303 B1 | 4/2003 | Van Tassel et al. |
| 6,579,303 B2 | 6/2003 | Amplatz |
| 6,585,748 B1 | 7/2003 | Jeffree |
| 6,589,256 B2 | 7/2003 | Forber |
| 6,589,265 B1 | 7/2003 | Palmer et al. |
| 6,599,308 B2 | 7/2003 | Amplatz |
| 6,605,102 B1 | 8/2003 | Mazzocchi et al. |
| 6,605,111 B2 | 8/2003 | Bose et al. |
| 6,607,539 B1 | 8/2003 | Hayashi et al. |
| 6,613,074 B1 | 9/2003 | Mitelberg |
| 6,626,939 B1 | 9/2003 | Burnside et al. |
| 6,632,241 B1 | 10/2003 | Hancock |
| 6,635,068 B1 | 10/2003 | Dubrul et al. |
| 6,638,257 B2 | 10/2003 | Amplatz |
| 6,652,556 B1 | 11/2003 | Van Tassel et al. |
| 6,666,882 B1 | 12/2003 | Bose et al. |
| 6,669,721 B1 | 12/2003 | Bose et al. |
| 6,682,546 B2 | 1/2004 | Amplatz |
| 6,689,150 B1 | 2/2004 | Van Tassel |
| 6,689,486 B2 | 2/2004 | Ho et al. |
| 6,719,778 B1 | 4/2004 | Van Tassel et al. |
| 6,730,119 B1 | 5/2004 | Smalling |
| 6,743,236 B2 | 6/2004 | Barry et al. |
| 6,743,251 B1 | 6/2004 | Eder |
| 6,746,468 B1 | 6/2004 | Sepetka et al. |
| 6,746,890 B2 | 6/2004 | Gupta et al. |
| 6,752,826 B2 | 6/2004 | Holloway et al. |
| 6,780,196 B2 | 8/2004 | Chin et al. |
| 6,811,560 B2 | 11/2004 | Jones et al. |
| 6,818,006 B2 | 11/2004 | Douk et al. |
| 6,855,153 B2 | 2/2005 | Saadat |
| 6,855,154 B2 | 2/2005 | Abdel-Gawwad |
| 6,878,384 B2 | 4/2005 | Cruise et al. |
| 6,936,055 B1 | 8/2005 | Ken et al. |
| 6,940,209 B2 | 9/2005 | Henderson |
| 6,953,472 B2 | 10/2005 | Palmer et al. |
| 6,953,473 B2 | 10/2005 | Porter |
| 6,966,892 B2 | 11/2005 | Gandhi et al. |
| 6,994,092 B2 | 2/2006 | van der Burg et al. |
| 7,001,409 B2 | 2/2006 | Amplatz |
| 7,004,962 B2 | 2/2006 | Stinson |
| 7,011,671 B2 | 3/2006 | Welch |
| 7,044,958 B2 | 5/2006 | Douk et al. |
| 7,052,513 B2 | 5/2006 | Thompson |
| 7,083,632 B2 | 8/2006 | Avellanet et al. |
| 7,101,390 B2 | 9/2006 | Nelson |
| 7,122,043 B2 | 10/2006 | Greenhalgh et al. |
| 7,128,736 B1 | 10/2006 | Abrams et al. |
| 7,179,276 B2 | 2/2007 | Barry et al. |
| 7,182,774 B2 | 2/2007 | Barry et al. |
| 7,195,636 B2 | 3/2007 | Avellanet et al. |
| 7,198,613 B2 | 4/2007 | Gandhi et al. |
| 7,201,918 B2 | 4/2007 | Cruise |
| 7,229,454 B2 | 6/2007 | Tran |
| 7,229,461 B2 | 7/2007 | Chin et al. |
| 7,275,471 B2 | 10/2007 | Nishri et al. |
| 7,326,225 B2 | 2/2008 | Ferrera et al. |
| 7,329,279 B2 | 2/2008 | Haug et al. |
| 7,331,980 B2 | 2/2008 | Dubrul |
| 7,410,482 B2 | 8/2008 | Murphy |
| 7,419,503 B2 | 9/2008 | Pulnev et al. |
| 7,490,396 B2 | 2/2009 | Bradley |
| 7,524,319 B2 | 4/2009 | Dubrul |
| 7,569,066 B2 | 8/2009 | Gerberding |
| 7,573,382 B2 | 8/2009 | Choubey et al. |
| 7,575,582 B2 | 8/2009 | Gandhi et al. |
| 7,578,826 B2 | 8/2009 | Gandhi et al. |
| 7,597,704 B2 | 10/2009 | Frazier et al. |
| 7,648,532 B2 | 1/2010 | Greenhalgh et al. |

(56) References Cited

U.S. PATENT DOCUMENTS

| | | |
|---|---|---|
| 7,695,488 B2 | 4/2010 | Berenstein |
| 7,722,637 B2 | 5/2010 | Barry et al. |
| 7,745,732 B2 | 6/2010 | Michael et al. |
| 7,806,919 B2 | 10/2010 | Bloom et al. |
| 7,862,577 B2 | 1/2011 | Gray et al. |
| 7,942,925 B2 | 5/2011 | Yodaf |
| 7,989,703 B2 | 8/2011 | Schaffer |
| 8,043,326 B2 | 10/2011 | Hancock |
| 8,043,329 B2 | 10/2011 | Khairkhahan |
| 8,066,757 B2 | 11/2011 | Ferrera et al. |
| 8,142,456 B2 | 3/2012 | Rosqueta et al. |
| 8,182,506 B2 | 5/2012 | Fitz et al. |
| 8,192,480 B2 | 6/2012 | Tieu et al. |
| 8,313,505 B2 | 11/2012 | Amplatz et al. |
| 8,377,091 B2 | 2/2013 | Cruise et al. |
| 8,398,670 B2 | 3/2013 | Amplatz |
| 8,430,012 B1 | 4/2013 | Marchand |
| 8,506,619 B2 | 8/2013 | Ortiz et al. |
| 8,551,132 B2 | 10/2013 | Eskridge et al. |
| 8,597,320 B2 | 12/2013 | Sepetka |
| 8,597,323 B1 | 12/2013 | Plaza et al. |
| 8,690,907 B1 | 4/2014 | Janardhan et al. |
| 8,715,338 B2 | 5/2014 | Frid |
| 8,728,117 B1 | 5/2014 | Janardhan et al. |
| 8,747,430 B2 | 6/2014 | Porter |
| 8,758,395 B2 | 6/2014 | Kleshinski et al. |
| 8,795,330 B1 | 8/2014 | Janardhan et al. |
| 8,840,735 B2 | 9/2014 | Schaffer |
| 8,845,679 B1 | 9/2014 | Janardhan et al. |
| 9,078,658 B2 | 7/2015 | Hewitt et al. |
| 9,198,668 B2 | 12/2015 | Theobald et al. |
| 9,198,670 B2 | 12/2015 | Hewitt et al. |
| 9,259,337 B2 | 2/2016 | Cox et al. |
| 9,272,323 B2 | 3/2016 | Schaffer |
| 9,295,473 B2 | 3/2016 | Hewitt et al. |
| 9,492,174 B2 | 11/2016 | Hewitt et al. |
| 9,504,588 B2 | 11/2016 | Sadisivan et al. |
| 9,597,087 B2 | 3/2017 | Marchand et al. |
| 9,629,635 B2 | 4/2017 | Hewitt et al. |
| 9,687,245 B2 | 6/2017 | Molaei et al. |
| 9,855,047 B2 | 1/2018 | Berez et al. |
| 9,955,976 B2 | 5/2018 | Hewitt et al. |
| 10,123,803 B2 | 11/2018 | Ferrera et al. |
| 10,130,372 B2 | 11/2018 | Griffin |
| 10,136,896 B2 | 11/2018 | Hewitt et al. |
| 10,238,393 B2 | 3/2019 | Marchand et al. |
| 10,260,182 B2 | 4/2019 | Thompson et al. |
| 10,260,183 B2 | 4/2019 | Marchand et al. |
| 10,398,441 B2 | 9/2019 | Warner et al. |
| 10,426,589 B2 | 10/2019 | Van der Burg et al. |
| 10,470,773 B2 | 11/2019 | Maguire et al. |
| 10,499,925 B2 | 12/2019 | Cruise et al. |
| 10,617,426 B2 | 4/2020 | Aboytes et al. |
| 10,716,573 B2 | 7/2020 | Connor |
| 10,736,758 B2 | 8/2020 | Ruvalcaba et al. |
| 10,813,645 B2 | 10/2020 | Hewitt et al. |
| 10,856,880 B1 | 12/2020 | Badruddin et al. |
| 10,952,739 B2 | 3/2021 | Plaza et al. |
| 11,033,277 B2 | 6/2021 | Wolfe et al. |
| 11,058,431 B2 | 7/2021 | Pereira et al. |
| 11,185,335 B2 | 11/2021 | Badruddin et al. |
| 11,202,636 B2 | 12/2021 | Zaidat et al. |
| 11,284,901 B2 | 3/2022 | Griffin |
| 11,389,174 B2 | 7/2022 | Griffin |
| 11,559,309 B2 | 1/2023 | Rangwala et al. |
| 2001/0031981 A1 | 10/2001 | Evans et al. |
| 2002/0065552 A1 | 5/2002 | Jayaraman et al. |
| 2002/0103542 A1 | 8/2002 | Bilbo |
| 2002/0111647 A1 | 8/2002 | Khairkhahan et al. |
| 2002/0143349 A1 | 10/2002 | Gifford, III et al. |
| 2002/0143361 A1 | 10/2002 | Douk et al. |
| 2002/0156499 A1 | 10/2002 | Konya et al. |
| 2002/0169473 A1 | 11/2002 | Sepetka et al. |
| 2002/0183787 A1 | 12/2002 | Wahr et al. |
| 2002/0187288 A1 | 12/2002 | Lim et al. |
| 2003/0012816 A1 | 1/2003 | West et al. |
| 2003/0028209 A1 | 2/2003 | Teoh et al. |
| 2003/0040771 A1 | 2/2003 | Hyodoh et al. |
| 2003/0171739 A1 | 9/2003 | Murphy et al. |
| 2003/0171774 A1 | 9/2003 | Freudenthal et al. |
| 2003/0181942 A1 | 9/2003 | Sutton et al. |
| 2003/0187473 A1 | 10/2003 | Berenstein et al. |
| 2003/0199913 A1 | 10/2003 | Dubrul et al. |
| 2004/0059370 A1 | 3/2004 | Green, Jr. et al. |
| 2004/0098027 A1 | 5/2004 | Tech et al. |
| 2004/0111147 A1 | 6/2004 | Rabkin et al. |
| 2004/0122367 A1 | 6/2004 | Sculati et al. |
| 2004/0143239 A1 | 7/2004 | Zhou et al. |
| 2004/0158311 A1 | 8/2004 | Berhow |
| 2004/0172053 A1 | 9/2004 | Barry et al. |
| 2004/0186562 A1 | 9/2004 | Cox |
| 2004/0193206 A1 | 9/2004 | Gerberding et al. |
| 2004/0193208 A1 | 9/2004 | Talpade et al. |
| 2004/0220563 A1 | 11/2004 | Eder |
| 2004/0260333 A1 | 12/2004 | Dubrul et al. |
| 2005/0021075 A1 | 1/2005 | Bonnette et al. |
| 2005/0033408 A1 | 2/2005 | Jones et al. |
| 2005/0053782 A1 | 3/2005 | Sen et al. |
| 2005/0096728 A1 | 5/2005 | Ramer |
| 2005/0112349 A1 | 5/2005 | Laurencin et al. |
| 2005/0113861 A1 | 5/2005 | Corcoran et al. |
| 2005/0113868 A1 | 5/2005 | Devellian et al. |
| 2005/0119684 A1 | 6/2005 | Gutterman et al. |
| 2005/0133046 A1 | 6/2005 | Becker et al. |
| 2005/0137623 A1 | 6/2005 | Jones et al. |
| 2005/0149173 A1 | 7/2005 | Hunter et al. |
| 2005/0216052 A1 | 9/2005 | Mazzocchi et al. |
| 2005/0222489 A1 | 10/2005 | Rahdert et al. |
| 2005/0228422 A1 | 10/2005 | Machold et al. |
| 2005/0228434 A1 | 10/2005 | Amplatz et al. |
| 2005/0267516 A1 | 12/2005 | Soleimani et al. |
| 2005/0277978 A1 | 12/2005 | Greenhalgh |
| 2006/0009798 A1 | 1/2006 | Callister et al. |
| 2006/0009799 A1 | 1/2006 | Kleshinski et al. |
| 2006/0009800 A1 | 1/2006 | Christianson et al. |
| 2006/0052815 A1 | 3/2006 | Fitz et al. |
| 2006/0052816 A1 | 3/2006 | Bates et al. |
| 2006/0064151 A1 | 3/2006 | Guterman et al. |
| 2006/0083721 A1 | 4/2006 | Cohen et al. |
| 2006/0106421 A1 | 5/2006 | Teoh |
| 2006/0116708 A1 | 6/2006 | Ogawa et al. |
| 2006/0135947 A1 | 6/2006 | Soltesz et al. |
| 2006/0155323 A1 | 7/2006 | Porter et al. |
| 2006/0178694 A1 | 8/2006 | Greenhalgh et al. |
| 2006/0200192 A1 | 9/2006 | Fitz et al. |
| 2006/0200234 A1 | 9/2006 | Hines |
| 2006/0212055 A1 | 9/2006 | Karabey et al. |
| 2006/0217799 A1 | 9/2006 | Mailander et al. |
| 2006/0235464 A1 | 10/2006 | Avellanet et al. |
| 2006/0247680 A1 | 11/2006 | Amplatz et al. |
| 2006/0252984 A1 | 11/2006 | Rahdert et al. |
| 2006/0253149 A1 | 11/2006 | Gandhi et al. |
| 2006/0271086 A1 | 11/2006 | Ramzipoor et al. |
| 2007/0021816 A1 | 1/2007 | Rudin |
| 2007/0031584 A1 | 2/2007 | Roth |
| 2007/0061006 A1 | 3/2007 | Desatnik et al. |
| 2007/0088387 A1 | 4/2007 | Eskridge et al. |
| 2007/0100419 A1 | 5/2007 | Licata et al. |
| 2007/0106323 A1 | 5/2007 | Barry et al. |
| 2007/0112380 A1 | 5/2007 | Figulla et al. |
| 2007/0142906 A1 | 6/2007 | Figulla et al. |
| 2007/0144124 A1 | 6/2007 | Schewe et al. |
| 2007/0167911 A1 | 7/2007 | Gandhi et al. |
| 2007/0167980 A1 | 7/2007 | Figulla et al. |
| 2007/0173928 A1 | 7/2007 | Morsi |
| 2007/0203062 A1 | 8/2007 | Ellis-Behnke et al. |
| 2007/0208373 A1 | 9/2007 | Zaver et al. |
| 2007/0208376 A1 | 9/2007 | Meng |
| 2007/0225760 A1 | 9/2007 | Moszner et al. |
| 2007/0233186 A1 | 10/2007 | Meng |
| 2007/0255388 A1 | 11/2007 | Rudakov et al. |
| 2007/0265656 A1 | 11/2007 | Amplatz et al. |
| 2007/0288083 A1 | 12/2007 | Hines |

(56) References Cited

U.S. PATENT DOCUMENTS

| | | |
|---|---|---|
| 2007/0299464 A1* | 12/2007 | Cruise ............. A61B 17/12168 128/831 |
| 2008/0033341 A1 | 2/2008 | Grad |
| 2008/0033366 A1 | 2/2008 | Matson |
| 2008/0033475 A1 | 2/2008 | Meng |
| 2008/0033478 A1 | 2/2008 | Meng |
| 2008/0097495 A1 | 4/2008 | Feller, III et al. |
| 2008/0119886 A1 | 5/2008 | Greenhalgh et al. |
| 2008/0161936 A1 | 7/2008 | Feller et al. |
| 2008/0188923 A1 | 8/2008 | Chu |
| 2008/0195139 A1 | 8/2008 | Donald et al. |
| 2008/0200945 A1 | 8/2008 | Amplatz et al. |
| 2008/0221600 A1 | 9/2008 | Dieck et al. |
| 2008/0228215 A1 | 9/2008 | Strauss et al. |
| 2008/0281350 A1 | 11/2008 | Sepetka et al. |
| 2009/0025820 A1 | 1/2009 | Adams |
| 2009/0062812 A1 | 3/2009 | Fitz et al. |
| 2009/0062834 A1 | 3/2009 | Moftakhar |
| 2009/0062841 A1 | 3/2009 | Amplatz et al. |
| 2009/0082803 A1 | 3/2009 | Adams et al. |
| 2009/0099647 A1 | 4/2009 | Glimsdale et al. |
| 2009/0112305 A1 | 4/2009 | Goldmann et al. |
| 2009/0132024 A1 | 5/2009 | Berkhoff |
| 2009/0163780 A1 | 6/2009 | Tieu |
| 2009/0227976 A1 | 9/2009 | Calabria |
| 2009/0275974 A1 | 11/2009 | Marchand |
| 2009/0287291 A1 | 11/2009 | Becking et al. |
| 2009/0287294 A1 | 11/2009 | Rosqueta et al. |
| 2009/0318948 A1 | 12/2009 | Linder et al. |
| 2010/0004679 A1 | 1/2010 | Osypka |
| 2010/0023048 A1 | 1/2010 | Mach |
| 2010/0023105 A1 | 1/2010 | Levy et al. |
| 2010/0069948 A1 | 3/2010 | Veznedaroglu et al. |
| 2010/0094409 A1 | 4/2010 | Barker et al. |
| 2010/0106235 A1 | 4/2010 | Kariniemi et al. |
| 2011/0022149 A1 | 1/2011 | Cox |
| 2011/0029008 A1 | 2/2011 | Gesswein |
| 2011/0046658 A1 | 2/2011 | Connor et al. |
| 2011/0046719 A1 | 2/2011 | Frid |
| 2011/0054515 A1 | 3/2011 | Bridgeman |
| 2011/0082493 A1 | 4/2011 | Samson et al. |
| 2011/0144669 A1 | 6/2011 | Becking et al. |
| 2011/0152823 A1 | 6/2011 | Mohiuddin et al. |
| 2011/0152993 A1 | 6/2011 | Marchand et al. |
| 2011/0202085 A1 | 8/2011 | Loganathan et al. |
| 2011/0208227 A1 | 8/2011 | Becking |
| 2011/0208233 A1 | 8/2011 | McGuckin |
| 2011/0224776 A1 | 9/2011 | Sepekta et al. |
| 2011/0295298 A1 | 12/2011 | Moszner |
| 2011/0319926 A1 | 12/2011 | Becking |
| 2012/0065667 A1 | 3/2012 | Javois et al. |
| 2012/0143237 A1 | 6/2012 | Cam |
| 2012/0165919 A1 | 6/2012 | Cox et al. |
| 2012/0197283 A1 | 8/2012 | Marchand et al. |
| 2012/0271337 A1 | 10/2012 | Figulla et al. |
| 2012/0283768 A1 | 11/2012 | Cox et al. |
| 2012/0330341 A1 | 12/2012 | Becking et al. |
| 2013/0066357 A1 | 3/2013 | Aboytes et al. |
| 2013/0092012 A1 | 4/2013 | Marchand et al. |
| 2013/0116722 A1 | 5/2013 | Aboytes et al. |
| 2013/0123830 A1 | 5/2013 | Becking et al. |
| 2013/0211495 A1 | 8/2013 | Halden et al. |
| 2013/0233160 A1 | 9/2013 | Marchand et al. |
| 2013/0239790 A1 | 9/2013 | Thompson et al. |
| 2013/0245667 A1 | 9/2013 | Marchand et al. |
| 2013/0268053 A1 | 10/2013 | Molaei et al. |
| 2013/0274862 A1 | 10/2013 | Cox et al. |
| 2013/0274863 A1 | 10/2013 | Cox et al. |
| 2013/0274866 A1 | 10/2013 | Cox et al. |
| 2013/0274868 A1 | 10/2013 | Cox et al. |
| 2013/0296912 A1 | 11/2013 | Ottma |
| 2013/0325051 A1 | 12/2013 | Martin et al. |
| 2014/0005713 A1 | 1/2014 | Bowman et al. |
| 2014/0005714 A1 | 1/2014 | Quick et al. |
| 2014/0018841 A1 | 1/2014 | Peiffer et al. |
| 2014/0052233 A1 | 2/2014 | Cox et al. |
| 2014/0058436 A1 | 2/2014 | Rosenbluth et al. |
| 2014/0074151 A1 | 3/2014 | Tischler et al. |
| 2014/0135734 A1 | 5/2014 | Dakin et al. |
| 2014/0135817 A1 | 5/2014 | Tischler et al. |
| 2014/0142611 A1 | 5/2014 | Plaza et al. |
| 2014/0172001 A1 | 6/2014 | Becking et al. |
| 2014/0200607 A1 | 7/2014 | Sepetka et al. |
| 2014/0257360 A1 | 9/2014 | Keillor |
| 2014/0257361 A1 | 9/2014 | Prom |
| 2014/0318354 A1 | 10/2014 | Thompson et al. |
| 2014/0318355 A1 | 10/2014 | Marchand et al. |
| 2014/0330299 A1* | 11/2014 | Rosenbluth ...... A61B 17/12154 606/191 |
| 2014/0358178 A1 | 12/2014 | Hewitt et al. |
| 2015/0012033 A1 | 1/2015 | Plaza et al. |
| 2015/0133989 A1 | 5/2015 | Lubock et al. |
| 2015/0182674 A1 | 7/2015 | Schaffer |
| 2015/0272589 A1 | 10/2015 | Lorenzo |
| 2015/0283363 A1 | 10/2015 | Hewitt et al. |
| 2015/0313605 A1 | 11/2015 | Griffin |
| 2015/0374483 A1 | 12/2015 | Janardhan et al. |
| 2016/0015396 A1 | 1/2016 | Cox et al. |
| 2016/0015398 A1 | 1/2016 | Hewitt et al. |
| 2016/0030052 A1 | 2/2016 | Cragg et al. |
| 2016/0045201 A1 | 2/2016 | Rosenbluth et al. |
| 2016/0100842 A1 | 4/2016 | Plaza et al. |
| 2016/0192941 A1 | 7/2016 | Hewitt et al. |
| 2016/0249934 A1 | 9/2016 | Hewitt et al. |
| 2016/0249935 A1 | 9/2016 | Hewitt et al. |
| 2016/0249937 A1 | 9/2016 | Marchand et al. |
| 2016/0262769 A1 | 9/2016 | Cragg et al. |
| 2016/0324528 A1 | 11/2016 | Hebert et al. |
| 2016/0324668 A1 | 11/2016 | Wallace et al. |
| 2016/0335757 A1 | 11/2016 | Florent et al. |
| 2016/0367260 A9 | 12/2016 | Hewitt et al. |
| 2017/0035437 A1* | 2/2017 | Sarge ............... A61B 17/12163 |
| 2017/0079792 A1 | 3/2017 | Rhee et al. |
| 2017/0088988 A1 | 3/2017 | Thompson et al. |
| 2017/0095254 A1 | 4/2017 | Hewitt et al. |
| 2017/0128077 A1 | 5/2017 | Hewitt et al. |
| 2017/0191195 A1 | 7/2017 | Marchand et al. |
| 2017/0224350 A1 | 8/2017 | Shimizu et al. |
| 2017/0245862 A1 | 8/2017 | Cox et al. |
| 2017/0258473 A1 | 9/2017 | Plaza et al. |
| 2018/0000489 A1 | 1/2018 | Marchand et al. |
| 2018/0070955 A1 | 3/2018 | Greene, Jr. et al. |
| 2018/0140305 A1 | 5/2018 | Connor |
| 2018/0153554 A1 | 6/2018 | Walzman |
| 2018/0185130 A1* | 7/2018 | Janardhan ............. B23K 26/14 |
| 2018/0206849 A1 | 7/2018 | Hewitt et al. |
| 2018/0206851 A1 | 7/2018 | Walzman |
| 2018/0271540 A1 | 9/2018 | Merritt et al. |
| 2018/0303486 A1 | 10/2018 | Rosenbluth et al. |
| 2018/0338767 A1 | 11/2018 | Dasnurkar et al. |
| 2019/0046209 A1 | 2/2019 | Plaza et al. |
| 2019/0059909 A1 | 2/2019 | Griffin |
| 2019/0192166 A1 | 6/2019 | Hewitt et al. |
| 2019/0192167 A1 | 6/2019 | Lorenzo |
| 2019/0209180 A1 | 7/2019 | Kealey et al. |
| 2019/0218696 A1 | 7/2019 | Thompson et al. |
| 2019/0223876 A1 | 7/2019 | Badruddin et al. |
| 2019/0223881 A1 | 7/2019 | Hewitt et al. |
| 2019/0269414 A1 | 9/2019 | Griffin |
| 2019/0298364 A1 | 10/2019 | Walsh et al. |
| 2019/0343533 A1 | 11/2019 | Costalat |
| 2019/0365385 A1 | 12/2019 | Gorochow et al. |
| 2020/0038035 A1 | 2/2020 | Griffin |
| 2020/0113576 A1 | 4/2020 | Gorochow et al. |
| 2020/0289124 A1 | 9/2020 | Rangwala et al. |
| 2020/0289125 A1 | 9/2020 | Dholakia et al. |
| 2020/0289126 A1 | 9/2020 | Hewitt et al. |
| 2021/0007754 A1 | 1/2021 | Milhous et al. |
| 2021/0128165 A1 | 5/2021 | Pulugurtha et al. |
| 2021/0153871 A1 | 5/2021 | Griffin |

(56) References Cited

U.S. PATENT DOCUMENTS

| | | |
|---|---|---|
| 2022/0323084 A1 | 2/2022 | Schiffer |
| 2022/0257260 A1 | 8/2022 | Hewitt et al. |

FOREIGN PATENT DOCUMENTS

| | | |
|---|---|---|
| CN | 106974691 | 7/2017 |
| EP | 0706876 | 7/2000 |
| EP | 0808138 | 5/2005 |
| EP | 1576929 | 9/2005 |
| EP | 1844717 | 10/2007 |
| EP | 1923019 | 5/2008 |
| EP | 2055263 | 6/2009 |
| EP | 2258275 | 12/2011 |
| EP | 2596754 | 5/2013 |
| EP | 2157937 | 3/2017 |
| FR | 2333169 | 6/1997 |
| JP | 52141092 | 11/1977 |
| JP | H4-47415 | 4/1992 |
| WO | WO 95/30384 | 11/1995 |
| WO | WO 1996/01591 | 1/1996 |
| WO | WO 1997/26939 | 7/1997 |
| WO | WO 1999/03404 | 1/1999 |
| WO | WO 1999/05977 | 2/1999 |
| WO | WO 1999/62432 | 12/1999 |
| WO | WO 01/45571 | 6/2001 |
| WO | WO 01/93782 | 12/2001 |
| WO | WO 02/00139 | 1/2002 |
| WO | WO 03/011151 | 2/2003 |
| WO | WO 03/032818 | 4/2003 |
| WO | WO 03/063732 | 8/2003 |
| WO | WO 2004/047649 | 6/2004 |
| WO | WO 2004/093742 | 11/2004 |
| WO | WO 2005/117718 | 12/2005 |
| WO | WO 2006/026744 | 3/2006 |
| WO | WO 2006/055683 | 5/2006 |
| WO | WO 2007/006139 | 1/2007 |
| WO | WO 2007/096183 | 8/2007 |
| WO | WO 2008/151204 | 12/2008 |
| WO | WO 2009/036219 | 3/2009 |
| WO | WO 2009/048700 | 4/2009 |
| WO | WO 2009/121006 | 10/2009 |
| WO | WO 2009/126747 | 10/2009 |
| WO | WO 2009/132045 | 10/2009 |
| WO | WO 2009/134337 | 11/2009 |
| WO | WO 2009/135166 | 11/2009 |
| WO | WO 2010/134914 | 11/2010 |
| WO | WO 2011/057002 | 5/2011 |
| WO | WO 2013/102848 | 7/2013 |
| WO | WO2013119332 * | 8/2013 ............. A61B 17/03 |
| WO | WO 2014/087245 | 6/2014 |
| WO | WO 2014/169261 | 10/2014 |
| WO | WO 2015/160721 | 10/2015 |
| WO | WO 2015/171268 | 11/2015 |
| WO | WO 2015/192019 | 12/2015 |
| WO | WO 2017/153603 | 9/2017 |
| WO | WO 2018/051187 | 3/2018 |
| WO | WO 2018/058033 | 3/2018 |
| WO | WO 2019/040494 | 2/2019 |

OTHER PUBLICATIONS

Allen et al., "Micromachine Wedge Stepping Motor," pp. 1-6, Nov. 12-20, 1998 ASME International Mechanical Engineering Congress, Anaheim, CA.
Altes et al., "Creation of Saccular Aneurysms in the Rabbit: A model Suitable for Testing Endovascular Devices," American Roentgen Ray Society, Feb. 2000, pp. 1-6.
Ansari et al., "Thrombosis of a Fusiform Intracranial Aneurysm Induced by Overlapping Neuroform Stents: Case Report," Neurosurgery, E950-E951 vol. 60, No. 5, May 2007, pp. 1-7.
Atritech Press Release, Minneapolis, Jun. 18, 2007 "Atritech Announces Intellectual Property Acquisition, Transaction Establishes Company as leader in Left Atrial Appendage Market." pp. 1-2.

Caroff, J. et al., "Woven Endobridge (WEB) Device for endovascular treatment of ruptured intracranial wide-neck aneurysms: a single-center experience," Neuroradiology, 56(9):755-761 (Sep. 2014).
Caroff, J. et al., "Role of C—Arm VasoCT in the Use of Endovascular WEB Flow Disruption in Intracranial Aneurysm Treatment," AJNR Am. J. Neuroradiol. 35(7):1353-1357 (Jul. 2014).
Colla, R. et al., "Treatment of Wide-Neck Basilar Tip Aneurysms Using the Web II Device," The Neuroradiology Journal 26(6):669-677 (Dec. 2013).
De Backer, O. et al., "Percutaneous left atrial appendage occlusion for stroke prevention in atrial fibrillation: an update," Open Heart, 4:1-14 (2013).
Ding, Y.H. et al., "The Woven EndoBridge: A New Aneurysm Occlusion Device," AJNR Am. J. Neruradiol. 32:607-611 (Mar. 2011).
Duerig, T.W., "The Use of Superelasticity in Modern Medicine," MRS Bulletin, pp. 101-104 (Feb. 2002).
Fiorella, D. et al., "Interobserver variability in the assessment of aneurysm occlusion with the WEB aneurysm embolization system," J. NeuroIntervent. Surg. Jul. 1, 2014, pii: neurintsurg-2014-011251. doi: 10.1136/neurintsurg-2014-011251 [Epub ahead of print], pp. 1-5.
Fort Wayne Metals HHS Tube brochure, p. 28-29 (2009), Fort Wayne, Indiana, www.oldsite.fwmetals.com.
Grabenwoger et al., "Endothelialization of Biosynthetic vascular Prosthesis After Laser Perforation," Ann Thorac Surg, 66:S110-S114 (1998).
Guider Softip XF Guide Catheters Brochure, Boston Scientific Corporation 2004, pp. 1-4.
Gupta et al., "Nitinol Thin Film Three Dimensional Devices-Fabrication and Applications," From: SMST-2003: Proceedings of the International Conference on Shape Memory and Superelastic Technologies Published: 2004, 1-8.
Hill et al., "Initial Results of the AMPLATZER® Vascular Plug in the treatment of Congenital Heart Disease," Technology and Services, Business Briefing: US Cardiology, pp. 1-3 (2004).
Jeffree et al., "The Porus, Guidewire-Directed, Detachable Aneurysm Liner: A New Concept in the Endovascular Treatment of Intracranial Aneurysms," AJNR Am J Neuradiol 20:774-779 (May 1999).
Kallmes et al., "A New Endoluminal, Flow-Disrupting Device for Treatment of Saccular Eneurysms," Stroke, Journal of the American Heart Association 38:1-7 (2007).
Klisch, J. et al., "The Woven EndoBridge Cerebral Aneurysm Embolization Device (Web II): initial clinical experience," Neuroradiology 53:599-607 (2011).
Kónya, A. et al., "Preliminary Results with a New Vascular Basket Occluder in Swine," JVIR, 10(8):1043-1049 (1999).
Kwon et al., "Preliminary Results of the Luna Aneurysm Embolization System in a Rabbit Model: A New Intrasaccular Aneurysm Occlusion Device," AJNR Am J Neuroradiol, 32:602-606 (Mar. 2011).
Lendlein, A. et al., "Shape-Memory Polymers," Angew. Chem. Int. Ed., 41:2034-2057 (2002).
Lendlein, A. et al., "Biodegradable, Elastic Shape-Memory Polymers for Potential Biomedical Applications," Science 296:1673-1676 (May 31, 2002).
Lieber, B.B. et al., "The Role of Blood Impulse in Cerebral Aneurysm Coil Compaction: Effect of Aneurysm Neck Size," IMECE2003-43099, Proceedings of IMECE '03, 2003 ASME International Mechanical Engineering Congress, Washington, D.C. (Nov. 15-21, 2003), pp. 1-2.
Liu, C. et al., "Review of progress in shape-memory polymers," J. Mater. Chem. 17:1543-1558 (2007).
Lubicz, B. et al., "WEB Device for Endovascular Treatment of Wide-Neck Bifurcation Aneurysms," AJNR Am. J. Neuroradiol. 34(6):1209-1214 (Jun.-Jul. 2013).
Lubicz, B. et al., "WEB-DL Endovascular Treatment of Wide-Neck Bifurcation Aneurysms: Short- and Midterm Results in a European Study," AJNR Am. J. Neuroradiol. 35(3):432-438 (Mar. 2014). doi: 10.3174/ajnr.A3869. Epub Jan. 23, 2014.

(56) References Cited

OTHER PUBLICATIONS

Major, S. et al., "Life of Nitinol Drawn Filed Wires with Ag or Au Core for Medical Application," *International Journal of Mechanics* 2(7):73-80 (2013).
Matinlinna et al., "An Introduction to Silanes and Their Clinical Applications in Dentistry," *The International Journal of Prosthodontics*, 17(2):155-164 (2004).
Mine et al., "Intrasaccular flow-diversion for treatment of intracranial aneurysms: the Woven EndoBridge," *Expert Rev. Med. Devices*11(3): 315-325 (May 2014). doi: 10.1586/17434440.2014.907741. Epub Apr. 2, 2014.
Nakayama et al., "Development of Microporous Covered Stents: Geometrical Design of the Luminal Surface," *The International Journal of Artificial Organs*, 28(6):600-608 (2005).
Nemat-Nasser, S et al., "Superelastic and cyclic response of NiTi SMA at various strain rates and temperatures," *Mechanics of Materials* 38:463-474 (2006).
Nishi et al., "Embolization of experimental aneurysms using a heparin-loaded stent graft with micropores," *Cardiovascular Radiation Medicine* 4:29-33 (2003).
Nishi et al., "Occlusion of Experimental Aneurysms with Heparin-Loaded, Microporous Stent Grafts," *Neurosurgery* 53(6):1397-1405 (Dec. 2003).
Papagiannaki, C. et al., "WEB Intrasaccular Flow Disruptor-Prospective, Multicenter Experience in 83 Patients with 85 Aneurysms," *AJNR Am. J. Neuroradiol.* 35(11):2106-2111 (Nov.-Dec. 2014). 35(11):2106-11. doi: 10.3174/ajnr.A4028. Epub Jul. 3, 2014.
Park, J. et al., "Percutaneous Left Atrial Appendage Transcatheter Occlusion (PLAATO) for Stroke Prevention in Atrial Fibrillation: 2-Year Outcome," *J Invasive. Cardiol.*, 21(9):446-450 (2009).
Pelton, A.R. et al., "Optimisation of processing and properties of medical grade Nitinol wire," *Min. Invas. Ther. & Allied Technol.* 9(1):107-118 (2000).
Pham, Q. et al., "Electrospinning of Polymeric Nanofibers for Tissue Engineering Applications: A Review," *Tissue Engr* 12(5):1197-1211 (1996).
Pierot, L. et al., "Intrasaccular Flow-Disruption Treatment of Intracranial Aneurysms: Preliminary Results of a Multicenter Clinical Study," *AJNR Am J Neuroradiol.* 33(7):1232-1238 (Aug. 2012). doi: 10.3174/ajnr.A3191. Epub Jun. 7, 2012.
Pierot, L. et al., "Endovascular WEB Flow Disruption in Middle Cerebral Artery Aneurysms: Preliminary Feasibility, Clinical, and Anatomical Results in a Multicenter Study," *Neurosurgery* 73(1):27-35 (Jul. 2013).
Pierot, L. et al., "Role, safety, and efficacy of WEB flow disruption: a review," *EJMINT* Invited Review, 2014: 1419000139 (May 8, 2014).
Peirot, L. et al., "WEB Treatment of Intracranial Aneurysms: Feasiblity, Complications, and 1-Month Safety Results with the WEB DL and WEB SL/SLS in the French Observatory," *AJNR Am J Neuroradiol.* Feb. 5, 2015 [Epub ehead ofprint] pp. 1-9.
Romero, J. et al., "Left Atrial Appendage Closure Devices," Clinical Medicine Insights: *Cardiology*, 8:45-52 (2014).
Rottiers, W. et al., "Shape Memory Materials and their applications," in Korolev's readings: conference proceedings, pp. 250-250 (2011).
Salamat et al., "Experimental Evaluation of a New Transcatheter Vascular Embolization Device in the Swine Model," *J Vasc Interv Radiol*, 12:301-311 (2002).
Schaffer, J.E. et al., "Engineering Characteristics of Drawn Filled Nitinol Tube," SMST-2003: Proceedings of the International Conference on Shape Memory and Superelastic Technologies (ASM International), pp. 109-118 (2004).
Schmitz-Rode, T. et al., "Self-expandable spindle for transcatheter vascular occlusion: in vivo experiments. Work in progress." *Radiology* 188:95-100 (Jul. 1993).
Simgen, A. et al., "Evaluation of a newly designed flow diverter for the treatment of intracranial aneurysms in an elastase-induced aneurysm model, in New Zealand white rabbits," *Neuroradiology* 56:129-137 (2014).
Spelle, L. et al., "Letter to the Editor," *Neuroradiol J.* Jun. 2014; 27(3):369. doi: 10.15274/NRJ-2014-10048. Epub Jun. 17, 2014, pp. 1-2.
Stoeckel, D. et al., "Self-expanding nitinol stents: material and design considerations," *Eur. Radiol.* 14:292-301 (2004).
Turk, A. et al., "Evaluation of the TriSpan Neck Bridge Device for the Treatment of Wide-Necked Aneurysms: An Experimental Study in Canines, Editorial Comment: An Experimental Study in Canines," *Stroke* 32:492-497 (Feb. 2001).
Wallner, A.K. et al., "Coiling after Treatment with the Woven EndoBridge Cerebral Aneurysm Embolization Device," *Interventional Neuroradiology* 18:208-212 (2012).
Yeow, W.L. et al., Device- and LAA-Specific Characteristics for Successful LAA Closures: Tips and Tricks, *Intervent. Cardiol. Clin.*, 3:239-254 (2014).
Zimmermann et al., "Patent Foramen Oval Closure With the SeptRx Device, Initial Experience with the First "In-Tunnel" Device," *JACC Cardiovascular Interventions* vol. 3, No. 9., 2010, pp. 1-2.
International Search Report and Written Opinion dated Oct. 31, 2008 for International Application No. PCT/US2008/065694.
International Search Report and Written Opinion dated Nov. 26, 2009 for International Application No. PCT/US2009/042592.
International Search Report and Written Opinion dated Jul. 28, 2011 for International Application No. PCT/US2010/055494.
International Search Report and Written Opinion dated Jul. 21, 2015 for International Application No. PCT/US2015/025609.
International Search Report and Written Opinion dated Jan. 11, 2016 for International Application No. PCT/US2015/025613.
International Search Report and Written Opinion dated Jun. 10, 2020 for International Application No. PCT/US2020/022275.
International Search Report and Written Opinion dated Jun. 11, 2020 for International Application No. PCT/US2020/022364.
International Search Report and Written Opinion dated Jun. 15, 2020 for International Application No. PCT/US2020/022319.
International Search Report and Written Opinion dated Jul. 24, 2020 for International Application No. PCT/US2020/022096.
Extended European Search Report dated Apr. 24, 2014, in EP Appl No. EP 08770070 filed Jun. 3, 2008.
Extended European Search Report dated Jul. 30, 2014, in EP Appl No. EP 10829110 filed Nov. 4, 2010.
Extended European Search Report dated Dec. 13, 2017, in EP Appl No. EP 15789225.8 filed Jun. 5, 2015.
Official Action dated Mar. 8, 2019, in JP Appl. No. 2016-562549 filed Jun. 5, 2015.

* cited by examiner

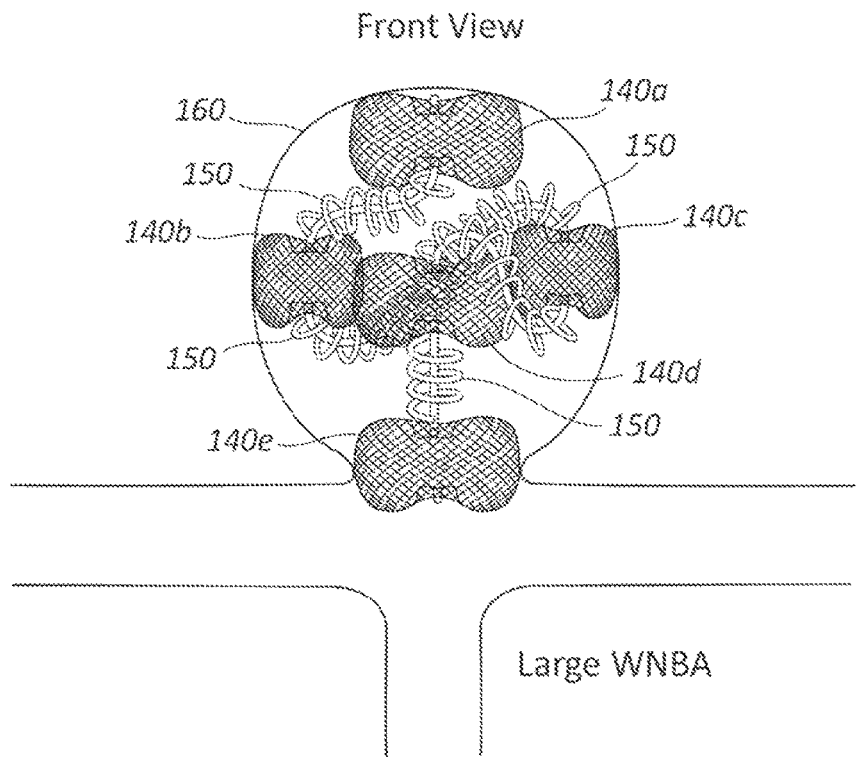
FIG. 14
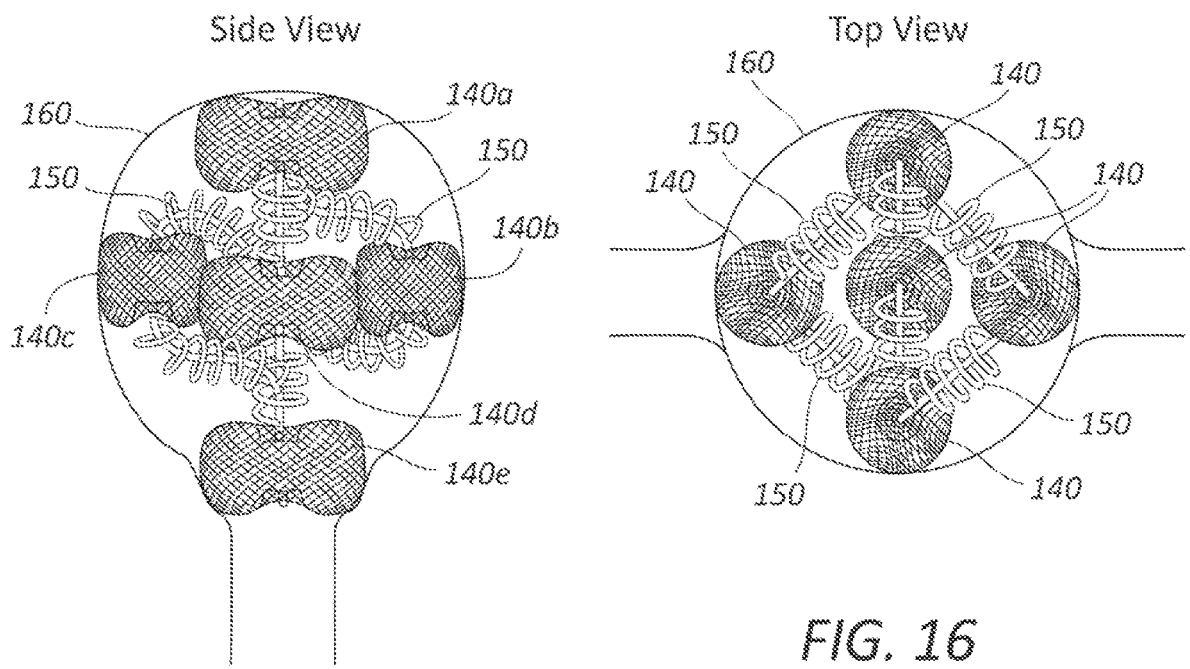
FIG. 15
FIG. 16

DEVICES HAVING MULTIPLE PERMEABLE SHELLS FOR TREATMENT OF VASCULAR DEFECTS

CROSS-REFERENCE TO RELATED APPLICATIONS

This application claims the benefit of priority under 35 U.S.C. § 119(e) from U.S. Provisional Application Ser. No. 62/988,076, filed Mar. 11, 2020, which is hereby incorporated by reference in its entirety for all purposes.

STATEMENT REGARDING FEDERALLY SPONSORED RESEARCH OR DEVELOPMENT

Not applicable.

FIELD OF THE INVENTION

Embodiments of devices and methods herein are directed to blocking a flow of fluid through a tubular vessel or into a small interior chamber of a saccular cavity or vascular defect within a mammalian body. More specifically, embodiments herein are directed to devices and methods for treatment of a vascular defect of a patient including some embodiments directed specifically to the treatment of cerebral aneurysms of patients.

BACKGROUND

The mammalian circulatory system is comprised of a heart, which acts as a pump, and a system of blood vessels which transport the blood to various points in the body. Due to the force exerted by the flowing blood on the blood vessel the blood vessels may develop a variety of vascular defects. One common vascular defect known as an aneurysm results from the abnormal widening of the blood vessel. Typically, vascular aneurysms are formed as a result of the weakening of the wall of a blood vessel and subsequent ballooning and expansion of the vessel wall. If, for example, an aneurysm is present within an artery of the brain, and the aneurysm should burst with resulting cranial hemorrhaging, death could occur.

Surgical techniques for the treatment of cerebral aneurysms typically involve a craniotomy requiring creation of an opening in the skull of the patient through which the surgeon can insert instruments to operate directly on the patient's brain. For some surgical approaches, the brain must be retracted to expose the parent blood vessel from which the aneurysm arises. Once access to the aneurysm is gained, the surgeon places a clip across the neck of the aneurysm thereby preventing arterial blood from entering the aneurysm. Upon correct placement of the clip the aneurysm will be obliterated in a matter of minutes. Surgical techniques may be effective treatment for many aneurysms. Unfortunately, surgical techniques for treating these types of conditions include major invasive surgical procedures which often require extended periods of time under anesthesia involving high risk to the patient. Such procedures thus require that the patient be in generally good physical condition in order to be a candidate for such procedures.

Various alternative and less invasive procedures have been used to treat cerebral aneurysms without resorting to major surgery. One approach to treating aneurysms without the need for invasive surgery involves the placement of sleeves or stents into the vessel and across the region where the aneurysm occurs. Such devices maintain blood flow through the vessel while reducing blood pressure applied to the interior of the aneurysm. Certain types of stents are expanded to the proper size by inflating a balloon catheter, referred to as balloon expandable stents, while other stents are designed to elastically expand in a self-expanding manner. Some stents are covered typically with a sleeve of polymeric material called a graft to form a stent-graft. Stents and stent-grafts are generally delivered to a preselected position adjacent a vascular defect through a delivery catheter. In the treatment of cerebral aneurysms, covered stents or stent-grafts have seen very limited use due to the likelihood of inadvertent occlusion of small perforator vessels that may be near the vascular defect being treated.

In addition, current uncovered stents are generally not sufficient as a stand-alone treatment. In order for stents to fit through the microcatheters used in small cerebral blood vessels, their density is usually reduced such that when expanded there is only a small amount of stent structure bridging the aneurysm neck. Thus, they do not block enough flow to cause clotting of the blood in the aneurysm and are thus generally used in combination with vaso-occlusive devices, such as the coils discussed above, to achieve aneurysm occlusion.

Some procedures involve the delivery of embolic or filling materials into an aneurysm. The delivery of such vaso-occlusion devices or materials may be used to promote hemostasis or fill an aneurysm cavity entirely. Vaso-occlusion devices may be placed within the vasculature of the human body, typically via a catheter, either to block the flow of blood through a vessel with an aneurysm through the formation of an embolus or to form such an embolus within an aneurysm stemming from the vessel. A variety of implantable, coil-type vaso-occlusion devices are known. The coils of such devices may themselves be formed into a secondary coil shape, or any of a variety of more complex secondary shapes. Vaso-occlusive coils are commonly used to treat cerebral aneurysms but suffer from several limitations including poor packing density, compaction due to hydrodynamic pressure from blood flow, poor stability in wide-necked aneurysms, and complexity and difficulty in the deployment thereof as most aneurysm treatments with this approach require the deployment of multiple coils. Coiling is less effective at treating certain physiological conditions, such as wide neck cavities (e.g., wide neck aneurysms) because there is a greater risk of the coils migrating out of the treatment site. Because there is a risk of the coils falling out of the aneurysm, a balloon or stent is typically also used along the neck of the aneurysm to provide a scaffold and help keep the coils within the target region-though even with these devices there is still a risk of the coils sticking out of the aneurysm.

A number of aneurysm neck bridging devices with defect spanning portions or regions have been attempted, however, none of these devices have had a significant measure of clinical success or usage. A major limitation in their adoption and clinical usefulness is the inability to position the defect spanning portion to assure coverage of the neck. Existing stent delivery systems that are neurovascular compatible (i.e., deliverable through a microcatheter and highly flexible) do not have the necessary rotational positioning capability. Another limitation of many aneurysm bridging devices described in the prior art is the poor flexibility. Cerebral blood vessels are tortuous, and a high degree of flexibility is required for effective delivery to most aneurysm locations in the brain.

What has been needed are devices and methods for delivery and use in small and tortuous blood vessels that can substantially block the flow of blood into an aneurysm, such as a cerebral aneurysm, with a decreased risk of inadvertent aneurysm rupture or blood vessel wall damage. In addition, what has been needed are methods and devices suitable for blocking blood flow in cerebral aneurysms over an extended period of time without a significant risk of deformation, compaction or dislocation.

Intrasaccular occlusive devices are part of a newer type of occlusion device used to treat various intravascular conditions including aneurysms. They are often more effective at treating these wide neck conditions, or larger treatment areas. The intrasaccular devices comprise a structure that sits within the aneurysm and provides an occlusive effect at the neck of the aneurysm to help limit blood flow into the aneurysm. The rest of the device comprises a relatively conformable structure that sits within the aneurysm helping to occlude all or a portion of the aneurysm. Intrasaccular devices typically conform to the shape of the treatment site. These devices also occlude the cross section of the neck of the treatment site/aneurysm, thereby promoting clotting and causing thrombosis and closing of the aneurysm over time.

Though intrasaccular devices offer some advantages in occluding target areas such as aneurysms, intrasaccular devices are not currently recommended for aneurysms having a diameter larger than 10 mm due to size restrictions. Intrasaccular devices or permeable shells having an expanded diameter over 11 mm have many issues, including challenges with delivery through microcatheters typically used to deliver these devices to cerebral aneurysms. Wide necked bifurcation aneurysms (WNBAs) are commonly located distal to the internal carotid artery (ICA) terminus and thus, neuro-interventional physicians treating the WNBA prefer devices with lower profile delivery systems. Because a larger number of wires and wires having larger diameters are required to create permeable shells having larger diameters (e.g., 11 mm or greater), such devices result in stiff and large profile delivery systems that can be difficult to navigate to distal intracranial locations. Thus, large and giant aneurysms, such as WNBAs cannot be currently treated with a single intrasaccular device. Furthermore, intrasaccular devices may be difficult to deploy in sidewall aneurysms because the delivery catheter has an odd approach angle, making deployment into the cavity difficult.

The following embodiments address these issues by utilizing intrasaccular concepts along with embolic coiling to effectively treat a treatment location.

SUMMARY

An embolic or occlusive device is described used to treat a variety of conditions, including aneurysms and neurovascular aneurysms.

In one embodiment, the embolic device includes multiple permeable shells that are connected with helical coils. In some embodiments, the helical coils can utilize hydrogel to augment the occlusive effect of these helical coils.

In other embodiments, a device for treatment of a patient's cerebral aneurysm includes a plurality of permeable shells, each having a proximal end, a distal end, a radially constrained elongated state configured for delivery within a catheter lumen, an expanded state with a longitudinally shortened configuration relative to the radially constrained state, and a plurality of elongate filaments that are woven together to form a mesh; and a plurality of coils, wherein each coil of the plurality of coils connects at least one pair of permeable shells in the plurality of permeable shells.

In other embodiments, a method for treating a cerebral aneurysm having an interior cavity and a neck is described. The method includes the step of advancing an implant in a microcatheter to a region of interest in a cerebral artery. The implant includes a plurality of permeable shells, each having a proximal end, a distal end, a radially constrained elongated state configured for delivery within a catheter lumen, an expanded state with a longitudinally shortened configuration relative to the radially constrained state, and a plurality of elongate filaments that are woven together to form a mesh; and a plurality of coils, wherein each coil of the plurality of coils connects at least one pair of permeable shells in the plurality of permeable shells. In some embodiments, the coils can further utilize hydrogel to augment the occlusive effect of the coils. The implant may then be deployed within the cerebral aneurysm, wherein each of the permeable shells of the plurality of permeable shells expands to its expanded state in the interior cavity of the aneurysm. The microcatheter is then withdrawn from the region of interest after the implant is deployed.

In other embodiments, a device for treatment of a patient's cerebral aneurysm includes a first permeable shell having a proximal end, a distal end, a radially constrained elongated state configured for delivery within a catheter lumen, an expanded state with a longitudinally shortened configuration relative to the radially constrained state, and a plurality of elongate filaments that are woven together to form a mesh; a second permeable shell having a proximal end, a distal end, a radially constrained elongated state configured for delivery within a catheter lumen, an expanded state with a longitudinally shortened configuration relative to the radially constrained state, and a plurality of elongate filaments that are woven together to form a mesh; and a first coil (which may include a hydrogel) coupling the proximal end of the first permeable shell to the distal end of the second permeable shell. The device may further include at least an additional permeable shell having a proximal end, a distal end, a radially constrained elongated state configured for delivery within a catheter lumen, an expanded state with a longitudinally shortened configuration relative to the radially constrained state, and a plurality of elongate filaments that are woven together to form a mesh; and at least an additional coil (which may include a hydrogel) coupling the proximal end of the second permeable shell to the distal end of the at least an additional permeable shell.

In other embodiments, a method for treating a cerebral aneurysm having an interior cavity and a neck is described. The method includes the step of advancing an implant in a microcatheter to a region of interest in a cerebral artery. The implant includes a first permeable shell having a proximal end, a distal end, a radially constrained elongated state configured for delivery within a catheter lumen, an expanded state with a longitudinally shortened configuration relative to the radially constrained state, and a plurality of elongate filaments that are woven together to form a mesh; a second permeable shell having a proximal end, a distal end, a radially constrained elongated state configured for delivery within a catheter lumen, an expanded state with a longitudinally shortened configuration relative to the radially constrained state, and a plurality of elongate filaments that are woven together to form a mesh; and a first coil (e.g., including a hydrogel) coupling the proximal end of the first permeable shell to the distal end of the second permeable shell. The implant is then deployed within the cerebral aneurysm, wherein each of the permeable shells of the plurality of permeable shells expands to its expanded state in the interior cavity of the aneurysm. The microcatheter is then withdrawn from the region of interest after the implant is deployed. The implant may include additional permeable shells connected together through a plurality of coils.

BRIEF DESCRIPTION OF THE DRAWINGS

FIG. 14 shows a front view of an embodiment of a device for treatment of a large wide necked bifurcation aneurysm.

FIG. 15 shows a side view of an embodiment of a device for treatment of a large wide necked bifurcation aneurysm.

FIG. 16 shows a top view of an embodiment of a device for treatment of a large wide necked bifurcation aneurysm.

DETAILED DESCRIPTION

Figure 1:
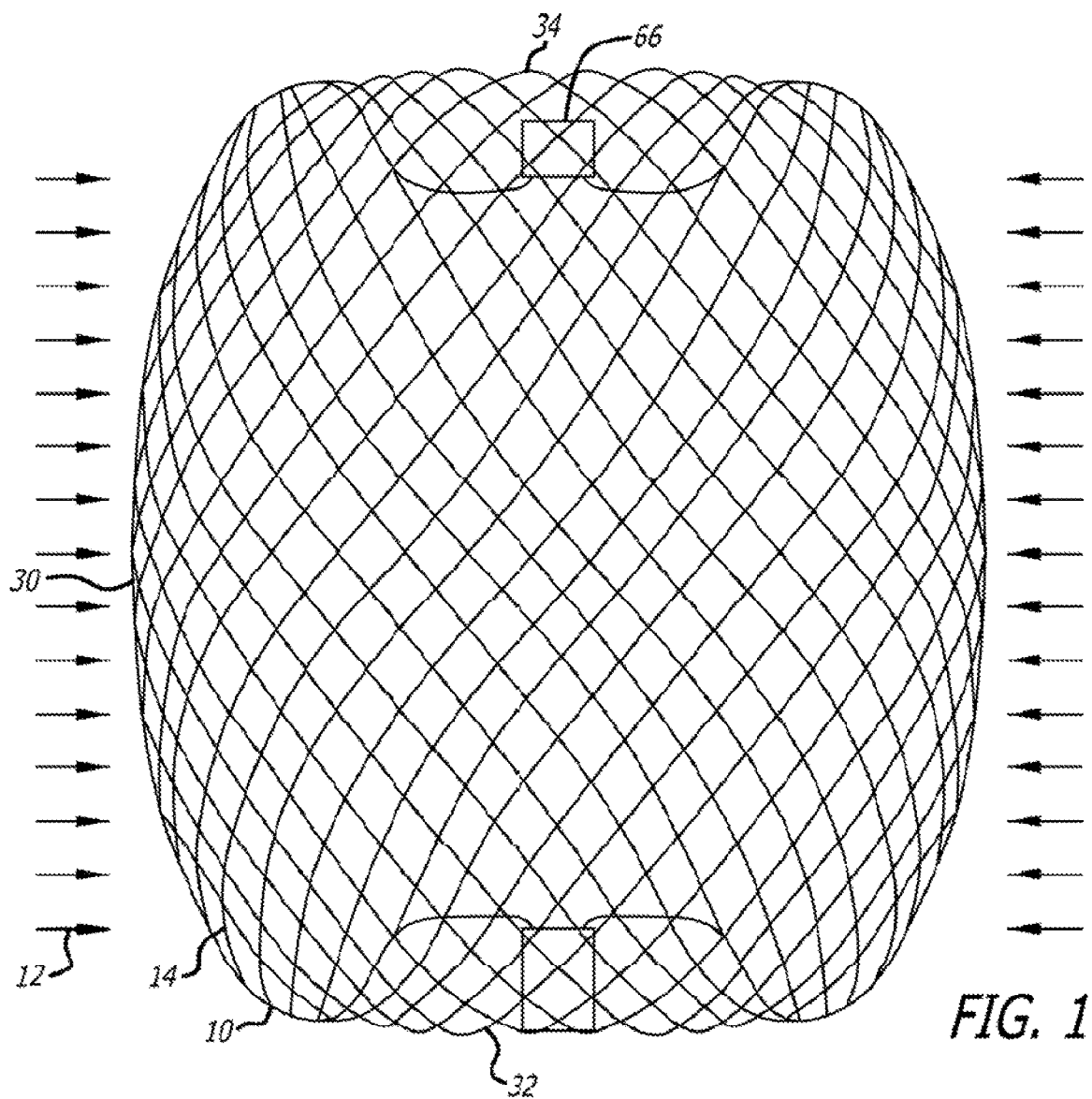
FIG. 1 is an elevation view of an embodiment of a device for treatment of a patient's vasculature and a plurality of arrows indicating inward radial force.

Discussed herein are devices and methods for the treatment of vascular defects that are suitable for minimally invasive deployment within a patient's vasculature, and particularly, within the cerebral vasculature of a patient. For such embodiments to be safely and effectively delivered to a desired treatment site and effectively deployed, some device embodiments may be configured for collapse to a low profile constrained state with a transverse dimension suitable for delivery through an inner lumen of a microcatheter and deployment from a distal end thereof. Embodiments of these devices may also maintain a clinically effective configuration with sufficient mechanical integrity once deployed so as to withstand dynamic forces within a patient's vasculature over time that may otherwise result in compaction of a deployed device. It may also be desirable for some device embodiments to acutely occlude a vascular defect of a patient during the course of a procedure in order to provide more immediate feedback regarding success of the treatment to a treating physician.

Intrasaccular occlusive devices that include a permeable shell formed from a woven or braided mesh have been described in US 2016/0249935, US 2017/0095254, US 2016/0249934, US 2016/0367260, US 2016/0249937, US 2018/0000489, and US 2019/0223881 all of which are hereby expressly incorporated by reference in their entirety for all purposes.

Some embodiments are particularly useful for the treatment of cerebral aneurysms by reconstructing a vascular wall so as to wholly or partially isolate a vascular defect from a patient's blood flow. Some embodiments may be configured to be deployed within a vascular defect to facilitate reconstruction, bridging of a vessel wall or both in order to treat the vascular defect. For some of these embodiments, the permeable shell of the device may be configured to anchor or fix the permeable shell in a clinically beneficial position. For some embodiments, the device may be disposed in whole or in part within the vascular defect in order to anchor or fix the device with respect to the vascular structure or defect. The permeable shell may be configured to span an opening, neck or other portion of a vascular defect in order to isolate the vascular defect, or a portion thereof, from the patient's nominal vascular system in order allow the defect to heal or to otherwise minimize the risk of the defect to the patient's health.

For some or all of the embodiments of devices for treatment of a patient's vasculature discussed herein, the permeable shell may be configured to allow some initial perfusion of blood through the permeable shell. The porosity of the permeable shell may be configured to sufficiently isolate the vascular defect so as to promote healing and isolation of the defect, but allow sufficient initial flow through the permeable shell so as to reduce or otherwise minimize the mechanical force exerted on the membrane the dynamic flow of blood or other fluids within the vasculature against the device. For some embodiments of devices for treatment of a patient's vasculature, only a portion of the permeable shell that spans the opening or neck of the vascular defect, sometimes referred to as a defect spanning portion, need be permeable and/or conducive to thrombus formation in a patient's bloodstream. For such embodiments, that portion of the device that does not span an opening or neck of the vascular defect may be substantially non-permeable or completely permeable with a pore or opening configuration that is too large to effectively promote thrombus formation.

In general, it may be desirable in some cases to use a hollow, thin walled device with a permeable shell of resilient material that may be constrained to a low profile for delivery within a patient. Such a device may also be configured to expand radially outward upon removal of the constraint such that the shell of the device assumes a larger volume and fills or otherwise occludes a vascular defect within which it is deployed. The outward radial expansion of the shell may serve to engage some or all of an inner surface of the vascular defect whereby mechanical friction between an outer surface of the permeable shell of the device and the inside surface of the vascular defect effectively anchors the device within the vascular defect. Some embodiments of such a device may also be partially or wholly mechanically captured within a cavity of a vascular defect, particularly where the defect has a narrow neck portion with a larger interior volume. In order to achieve a low profile and volume for delivery and be capable of a high ratio of expansion by volume, some device embodiments include a matrix of woven or braided filaments that are coupled together by the interwoven structure so as to form a self-expanding permeable shell having a pore or opening pattern between couplings or intersections of the filaments that is substantially regularly spaced and stable, while still allowing for conformity and volumetric constraint.

As used herein, the terms woven and braided are used interchangeably to mean any form of interlacing of filaments to form a mesh structure. In the textile and other industries, these terms may have different or more specific meanings depending on the product or application such as whether an article is made in a sheet or cylindrical form. For purposes of the present disclosure, these terms are used interchangeably.

For some embodiments, three factors may be critical for a woven or braided wire occlusion device for treatment of a patient's vasculature that can achieve a desired clinical outcome in the endovascular treatment of cerebral aneurysms. We have found that for effective use in some applications, it may be desirable for the implant device to have sufficient radial stiffness for stability, limited pore size for near-complete acute (intra-procedural) occlusion and a collapsed profile which is small enough to allow insertion through an inner lumen of a microcatheter. A device with a radial stiffness below a certain threshold may be unstable and may be at higher risk of embolization in some cases. Larger pores between filament intersections in a braided or woven structure may not generate thrombus and occlude a vascular defect in an acute setting and thus may not give a treating physician or health professional such clinical feedback that the flow disruption will lead to a complete and lasting occlusion of the vascular defect being treated. Delivery of a device for treatment of a patient's vasculature through a standard microcatheter may be highly desirable to allow access through the tortuous cerebral vasculature in the manner that a treating physician is accustomed. A detailed discussion of radial stiffness, pore size, and the necessary collapsed profile can be found in US 2017/0095254, which was previously expressly incorporated by reference in its entirety.

As has been discussed, some embodiments of devices for treatment of a patient's vasculature call for sizing the device which approximates (or with some over-sizing) the vascular site dimensions to fill the vascular site. One might assume that scaling of a device to larger dimensions and using larger filaments would suffice for such larger embodiments of a device. However, for the treatment of brain aneurysms, the diameter or profile of the radially collapsed device is limited by the catheter sizes that can be effectively navigated within the small, tortuous vessels of the brain. Further, as a device is made larger with a given or fixed number of resilient filaments having a given size or thickness, the pores or openings between junctions of the filaments are correspondingly larger. In addition, for a given filament size the flexural modulus or stiffness of the filaments and thus the structure decrease with increasing device dimension. Flexural modulus may be defined as the ratio of stress to strain. Thus, a device may be considered to have a high flexural modulus or be stiff if the strain (deflection) is low under a given force. A stiff device may also said to have low compliance.

Figure 2:
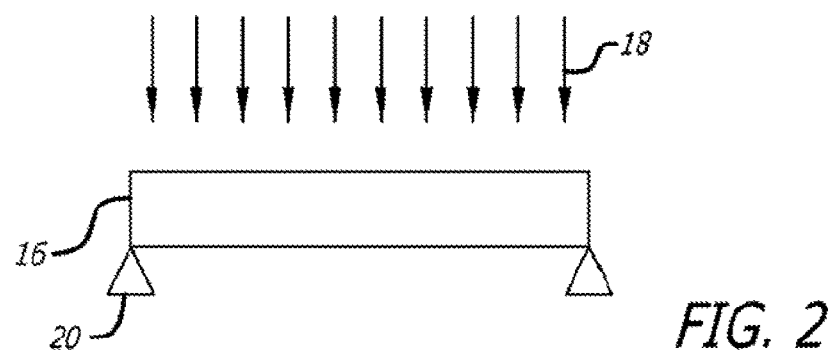
FIG. 2 is an elevation view of a beam supported by two simple supports and a plurality of arrows indicating force against the beam.
Figure 3:
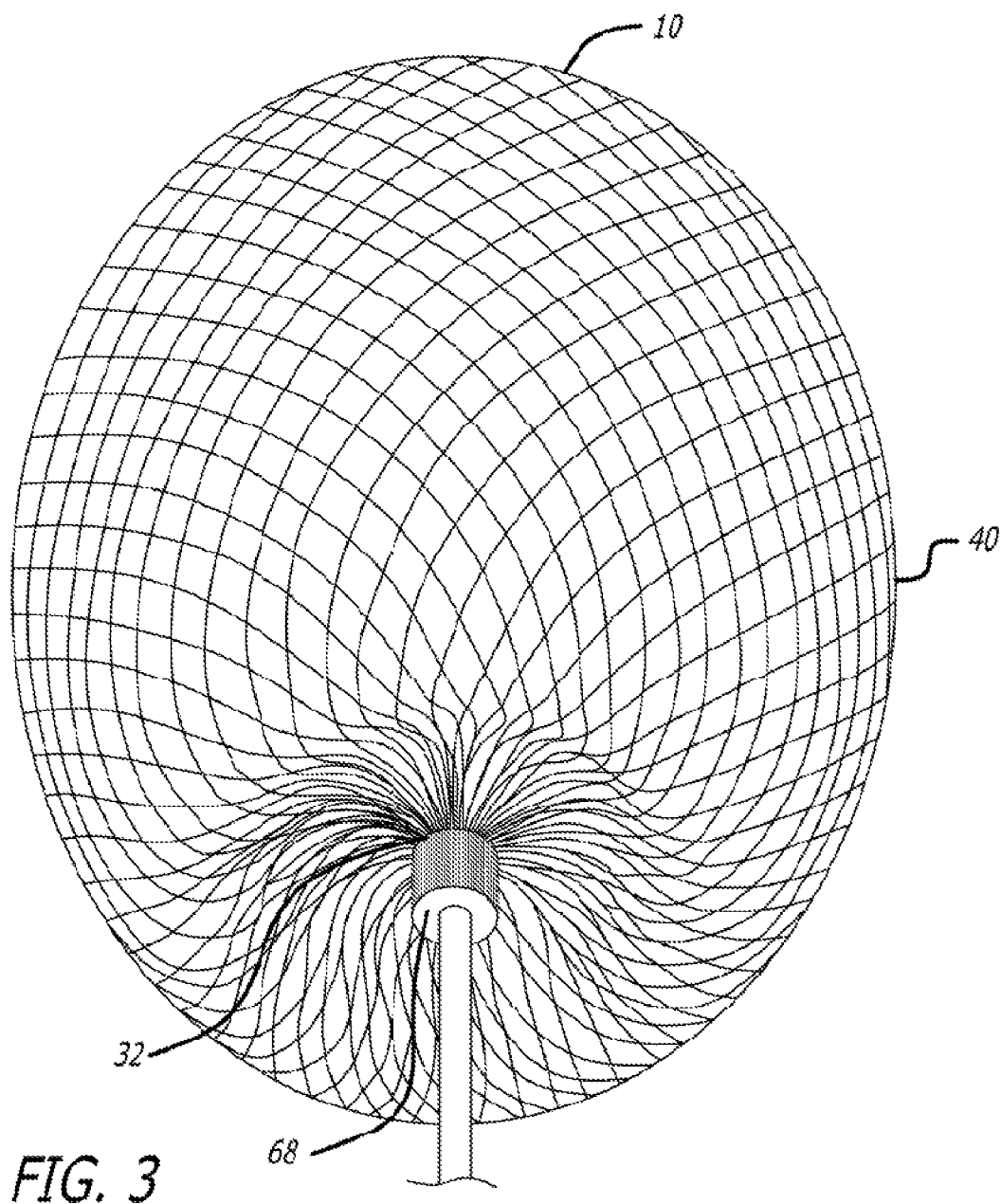
FIG. 3 is a bottom perspective view of an embodiment of a device for treatment of a patient's vasculature.

To properly configure larger size devices for treatment of a patient's vasculature, it may be useful to model the force on a device when the device is deployed into a vascular site or defect, such as a blood vessel or aneurysm, that has a diameter or transverse dimension that is smaller than a nominal diameter or transverse dimension of the device in a relaxed unconstrained state. As discussed, it may be advisable to "over-size" the device in some cases so that there is a residual force between an outside surface of the device and an inside surface of the vascular wall. The inward radial force on a device 10 that results from over-sizing is illustrated schematically in FIG. 1 with the arrows 12 in the figure representing the inward radial force. As shown in FIG. 2, these compressive forces on the filaments 14 of the device in FIG. 1 can be modeled as a simply supported beam 16 with a distributed load or force as show by the arrows 18 in the figure. It can be seen from the equation below for the deflection of a beam with two simple supports 20 and a distributed load that the deflection is a function of the length, L to the $4^{th}$ power:

$$\text{Deflection of Beam} = 5FL^4/384EI$$

where F=force,
L=length of beam,
E=Young's Modulus, and
I=moment of inertia.

Thus, as the size of the device increases and L increases, the compliance increases substantially. Accordingly, an outward radial force exerted by an outside surface of the filaments 14 of the device 10 against a constraining force when inserted into a vascular site such as blood vessel or aneurysm is lower for a given amount of device compression or over-sizing. This force may be important in some applications to assure device stability and to reduce the risk of migration of the device and potential distal embolization.

In some embodiments, a combination of small and large filament sizes may be utilized to make a device with a desired radial compliance and yet have a collapsed profile which is configured to fit through an inner lumen of commonly used microcatheters. A device fabricated with even a small number of relatively large filaments 14 can provide reduced radial compliance (or increased stiffness) compared to a device made with all small filaments. Even a relatively small number of larger filaments may provide a substantial increase in bending stiffness due to change in the moment of Inertia that results from an increase in diameter without increasing the total cross sectional area of the filaments. The moment of inertia (I) of a round wire or filament may be defined by the equation:

$$I = \pi d^4/64$$

where d is the diameter of the wire or filament.

Since the moment of inertia is a function of filament diameter to the fourth power, a small change in the diameter greatly increases the moment of inertia. Thus, small changes in filament size can have substantial impact on the deflection at a given load and thus the compliance of the device.

Thus, the stiffness can be increased by a significant amount without a large increase in the cross sectional area of a collapsed profile of the device 10. This may be particularly important as device embodiments are made larger to treat large aneurysms. While large cerebral aneurysms may be relatively rare, they present an important therapeutic challenge as some embolic devices currently available to physicians have relatively poor results compared to smaller aneurysms.

As such, some embodiments of devices for treatment of a patient's vasculature may be formed using a combination of filaments 14 with a number of different diameters such as 2, 3, 4, 5 or more different diameters or transverse dimensions. In device embodiments where filaments with two different diameters are used, some larger filament embodiments may have a transverse dimension of about 0.001 inches to about 0.004 inches and some small filament embodiments may have a transverse dimension or diameter of about 0.0004 inches and about 0.0015 inches, more specifically, about 0.0004 inches to about 0.001 inches. The ratio of the number of large filaments to the number of small filaments may be between about 2 and 12 and may also be between about 4 and 8. In some embodiments, the difference in diameter or transverse dimension between the larger and smaller filaments may be less than about 0.004 inches, more specifically, less than about 0.0035 inches, and even more specifically, less than about 0.002 inches.

As discussed above, device embodiments 10 for treatment of a patient's vasculature may include a plurality of wires, fibers, threads, tubes or other filamentary elements that form a structure that serves as a permeable shell. For some embodiments, a globular shape may be formed from such filaments by connecting or securing the ends of a tubular braided structure. For such embodiments, the density of a braided or woven structure may inherently increase at or near the ends where the wires or filaments 14 are brought together and decrease at or near a middle portion 30 disposed between a proximal end 32 and distal end 34 of the permeable shell 40. For some embodiments, an end or any other suitable portion of a permeable shell 40 may be positioned in an opening or neck of a vascular defect such as an aneurysm for treatment. As such, a braided or woven filamentary device with a permeable shell may not require the addition of a separate defect spanning structure having properties different from that of a nominal portion of the permeable shell to achieve hemostasis and occlusion of the vascular defect. Such a filamentary device may be fabricated by braiding, weaving or other suitable filament fabrication techniques. Such device embodiments may be shape set into a variety of three-dimensional shapes such as discussed herein.

Referring to FIGS. 3-10, an embodiment of a device for treatment of a patient's vasculature 10 is shown. The device 10 includes a self-expanding resilient permeable shell 40 having a proximal end 32, a distal end 34, a longitudinal axis 46 and further comprising a plurality of elongate resilient filaments 14 including large filaments 48 and small filaments 50 of at least two different transverse dimensions as shown in more detail in FIGS. 5, 7, and 18. The filaments 14 have a woven structure and are secured relative to each other at proximal ends 60 and distal ends 62 thereof. The permeable shell 40 of the device has a radially constrained elongated state configured for delivery within a microcatheter 61, as shown in FIG. 11, with the thin woven filaments 14 extending longitudinally from the proximal end 42 to the distal end 44 radially adjacent each other along a length of the filaments.

As shown in FIGS. 3-6, the permeable shell 40 also has an expanded relaxed state with a globular and longitudinally shortened configuration relative to the radially constrained state. In the expanded state, the woven filaments 14 form the self-expanding resilient permeable shell 40 in a smooth path radially expanded from a longitudinal axis 46 of the device between the proximal end 32 and distal end 34. The woven structure of the filaments 14 includes a plurality of openings 64 in the permeable shell 40 formed between the woven filaments. For some embodiments, the largest of said openings 64 may be configured to allow blood flow through the openings only at a velocity below a thrombotic threshold velocity. Thrombotic threshold velocity has been defined, at least by some, as the time-average velocity at which more than 50% of a vascular graft surface is covered by thrombus when deployed within a patient's vasculature. In the context of aneurysm occlusion, a slightly different threshold may be appropriate. Accordingly, the thrombotic threshold velocity as used herein shall include the velocity at which clotting occurs within or on a device, such as device 10, deployed within a patient's vasculature such that blood flow into a vascular defect treated by the device is substantially blocked in less than about 1 hour or otherwise during the treatment procedure. The blockage of blood flow into the vascular defect may be indicated in some cases by minimal contrast agent entering the vascular defect after a sufficient amount of contrast agent has been injected into the patient's vasculature upstream of the implant site and visualized as it dissipates from that site. Such sustained blockage of flow within less than about 1 hour or during the duration of the implantation procedure may also be referred to as acute occlusion of the vascular defect.

As such, once the device 10 is deployed, any blood flowing through the permeable shell may be slowed to a velocity below the thrombotic threshold velocity and thrombus will begin to form on and around the openings in the permeable shell 40. Ultimately, this process may be configured to produce acute occlusion of the vascular defect within which the device 10 is deployed. For some embodiments, at least the distal end of the permeable shell 40 may have a reverse bend in an everted configuration such that the secured distal ends 62 of the filaments 14 are withdrawn axially within the nominal permeable shell structure or contour in the expanded state. For some embodiments, the proximal end of the permeable shell further includes a reverse bend in an everted configuration such that the secured proximal ends 60 of the filaments 14 are withdrawn axially within the nominal permeable shell structure 40 in the expanded state. As used herein, the term everted may include a structure that is everted, partially everted and/or recessed with a reverse bend as shown in the device embodiment of FIGS. 3-6. For such embodiments, the ends 60 and 62 of the filaments 14 of the permeable shell or hub structure disposed around the ends may be withdrawn within or below the globular shaped periphery of the permeable shell of the device.

The elongate resilient filaments 14 of the permeable shell 40 may be secured relative to each other at proximal ends 60 and distal ends 62 thereof by one or more methods including welding, soldering, adhesive bonding, epoxy bonding or the like. In addition to the ends of the filaments being secured together, a distal hub 66 may also be secured to the distal ends 62 of the thin filaments 14 of the permeable shell 40 and a proximal hub 68 secured to the proximal ends 60 of the thin filaments 14 of the permeable shell 40. The proximal hub 68 may include a cylindrical member that extends proximally beyond the proximal ends 60 of the thin filaments so as to form a cavity 70 within a proximal portion of the proximal hub 68. The proximal cavity 70 may be used for holding adhesives such as epoxy, solder or any other suitable bonding agent for securing an elongate detachment tether 72 that may in turn be detachably secured to a delivery apparatus such as is shown in FIG. 11.

For some embodiments, the elongate resilient filaments 14 of the permeable shell 40 may have a transverse cross section that is substantially round in shape and be made from a superelastic material that may also be a shape memory metal. The shape memory metal of the filaments of the permeable shell 40 may be heat set in the globular configuration of the relaxed expanded state as shown in FIGS. 3-6. Suitable superelastic shape memory metals may include alloys such as NiTi alloy and the like. The superelastic properties of such alloys may be useful in providing the resilient properties to the elongate filaments 14 so that they can be heat set in the globular form shown, fully constrained for delivery within an inner lumen of a microcatheter and then released to self expand back to substantially the original heat set shape of the globular configuration upon deployment within a patient's body.

The device 10 may have an everted filamentary structure with a permeable shell 40 having a proximal end 32 and a distal end 34 in an expanded relaxed state. The permeable shell 40 has a substantially enclosed configuration for the embodiments shown. Some or all of the permeable shell 40 of the device 10 may be configured to substantially block or impede fluid flow or pressure into a vascular defect or otherwise isolate the vascular defect over some period of time after the device is deployed in an expanded state. The permeable shell 40 and device 10 generally also has a low profile, radially constrained state, as shown in FIG. 11, with an elongated tubular or cylindrical configuration that includes the proximal end 32, the distal end 34 and a longitudinal axis 46. While in the radially constrained state, the elongate flexible filaments 14 of the permeable shell 40 may be disposed substantially parallel and in close lateral proximity to each other between the proximal end and distal end forming a substantially tubular or compressed cylindrical configuration.

Figure 4:
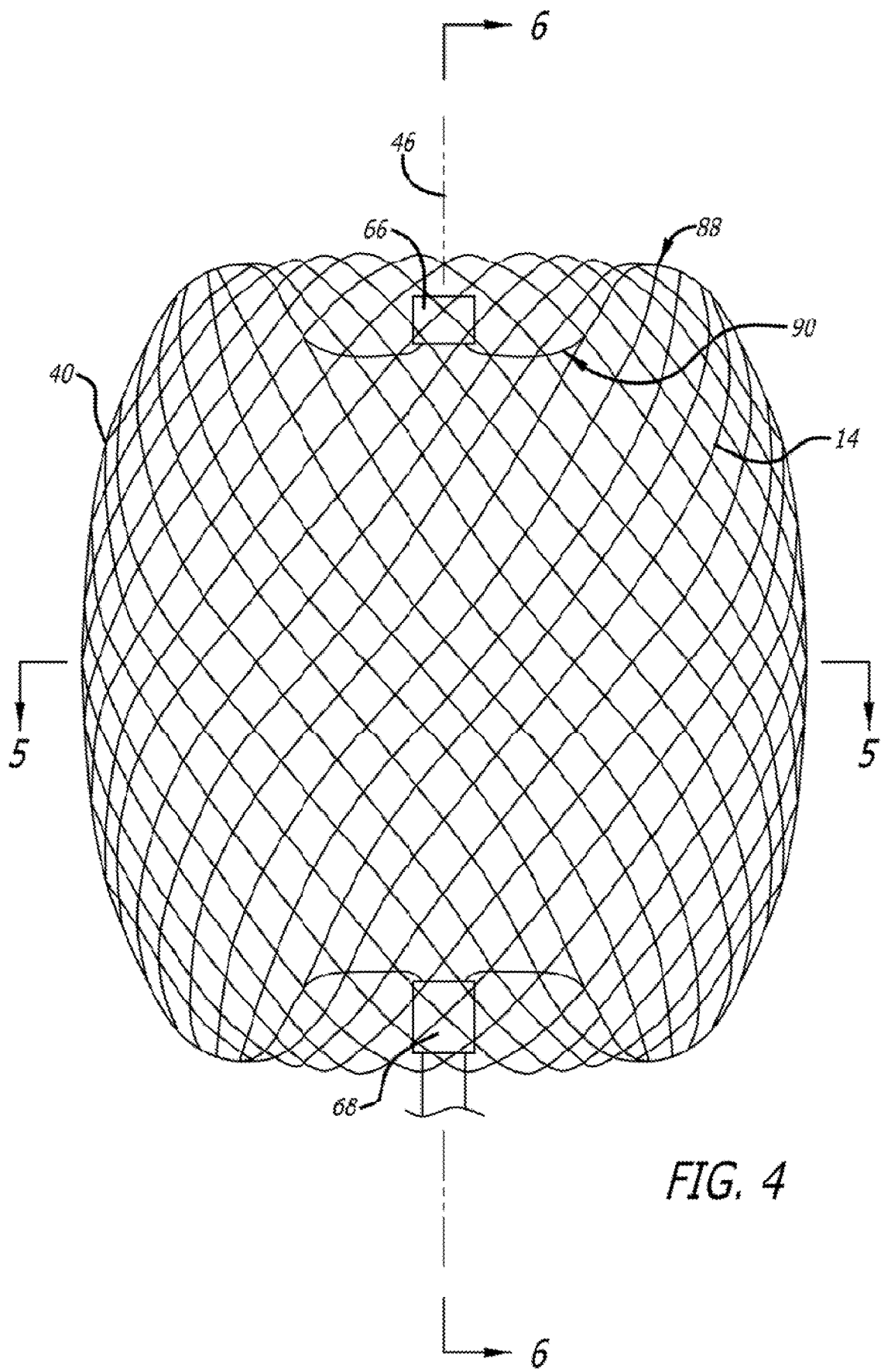
FIG. 4 is an elevation view of the device for treatment of a patient's vasculature of FIG. 3.
Figure 5:
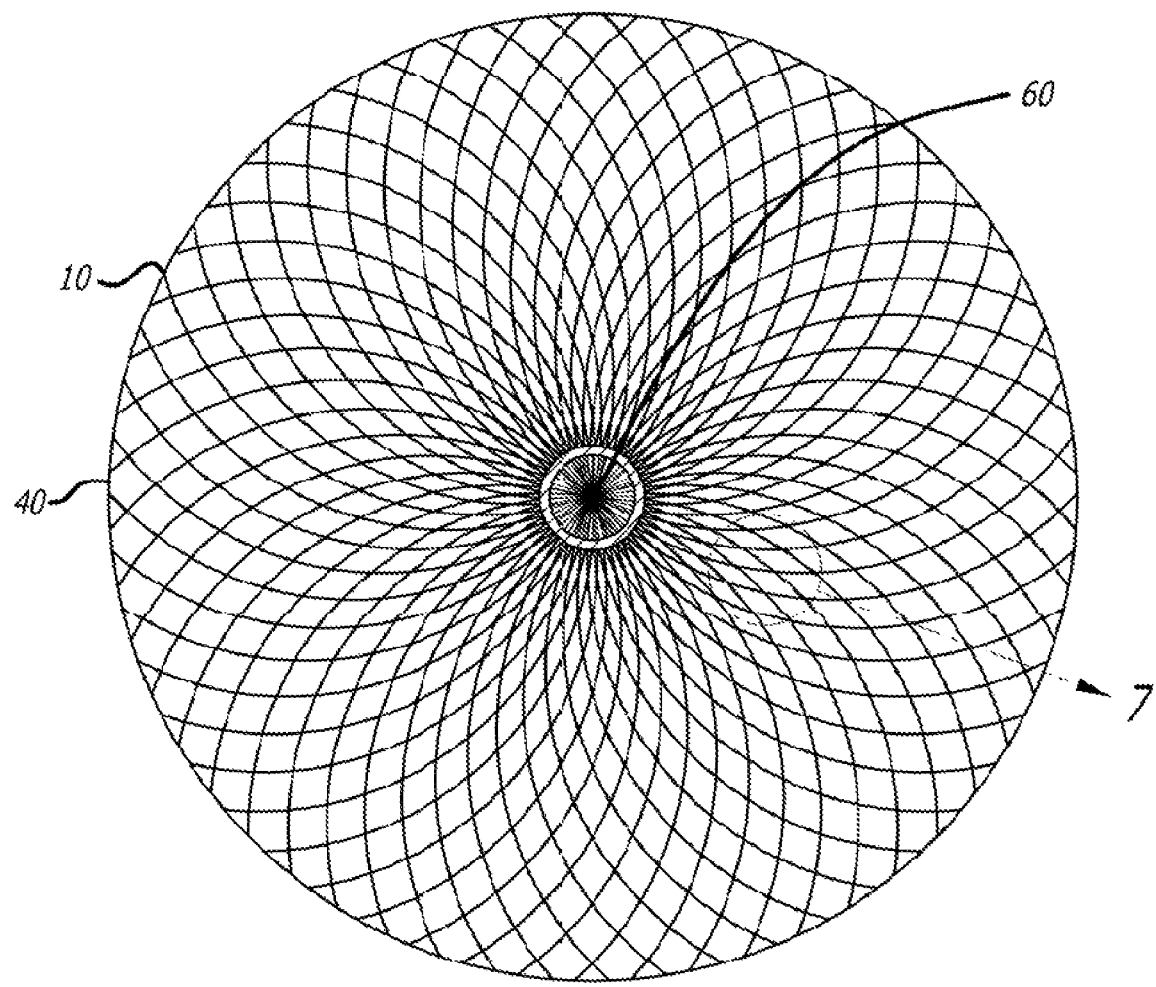
FIG. 5 is a transverse cross sectional view of the device of FIG. 4 taken along lines 5-5 in FIG. 4.

Proximal ends 60 of at least some of the filaments 14 of the permeable shell 40 may be secured to the proximal hub 68 and distal ends 62 of at least some of the filaments 14 of the permeable shell 40 are secured to the distal hub 66, with the proximal hub 68 and distal hub 66 being disposed substantially concentric to the longitudinal axis 46 as shown in FIG. 4. The ends of the filaments 14 may be secured to the respective hubs 66 and 68 by any of the methods discussed above with respect to securement of the filament ends to each other, including the use of adhesives, solder, welding and the like. A middle portion 30 of the permeable shell 40 may have a first transverse dimension with a low profile suitable for delivery from a microcatheter as shown in FIG. 11. Radial constraint on the device 10 may be applied by an inside surface of the inner lumen of a microcatheter, such as the distal end portion of the microcatheter 61 shown, or it may be applied by any other suitable mechanism that may be released in a controllable manner upon ejection of the device 10 from the distal end of the catheter. In FIG. 11 a proximal end or hub 68 of the device 10 is secured to a distal end of an elongate delivery apparatus 111 of a delivery system 112 disposed at the proximal hub 68 of the device 10. Additional details of delivery devices can be found in, e.g., US 2016/0367260, which was previously incorporated by reference in its entirety.

Some device embodiments 10 having a braided or woven filamentary structure may be formed using about 10 filaments to about 300 filaments 14, more specifically, about 10 filaments to about 100 filaments 14, and even more specifically, about 60 filaments to about 80 filaments 14. Some embodiments of a permeable shell 40 may include about 70 filaments to about 300 filaments extending from the proximal end 32 to the distal end 34, more specifically, about 100 filaments to about 200 filaments extending from the proximal end 32 to the distal end 34. For some embodiments, the filaments 14 may have a transverse dimension or diameter of about 0.0008 inches to about 0.004 inches. The elongate resilient filaments 14 in some cases may have an outer transverse dimension or diameter of about 0.0005 inch to about 0.005 inch, more specifically, about 0.001 inch to about 0.003 inch, and in some cases about 0.0004 inches to about 0.002 inches. For some device embodiments 10 that include filaments 14 of different sizes, the large filaments 48 of the permeable shell 40 may have a transverse dimension or diameter that is about 0.001 inches to about 0.004 inches and the small filaments 50 may have a transverse dimension or diameter of about 0.0004 inches to about 0.0015 inches, more specifically, about 0.0004 inches to about 0.001 inches. In addition, a difference in transverse dimension or diameter between the small filaments 50 and the large filaments 48 may be less than about 0.004 inches, more specifically, less than about 0.0035 inches, and even more specifically, less than about 0.002 inches. For embodiments of permeable shells 40 that include filaments 14 of different sizes, the number of small filaments 50 of the permeable shell 40 relative to the number of large filaments 48 of the permeable shell 40 may be about 2 to 1 to about 15 to 1, more specifically, about 2 to 1 to about 12 to 1, and even more specifically, about 4 to 1 to about 8 to 1.

The expanded relaxed state of the permeable shell 40, as shown in FIG. 4, has an axially shortened configuration relative to the constrained state such that the proximal hub 68 is disposed closer to the distal hub 66 than in the constrained state. Both hubs 66 and 68 are disposed substantially concentric to the longitudinal axis 46 of the device and each filamentary element 14 forms a smooth arc between the proximal and distal hubs 66 and 68 with a reverse bend at each end. A longitudinal spacing between the proximal and distal hubs 66 and 68 of the permeable shell 40 in a deployed relaxed state may be about 25 percent to about 75 percent of the longitudinal spacing between the proximal and distal hubs 66 and 68 in the constrained cylindrical state, for some embodiments. The arc of the filaments 14 between the proximal and distal ends 32 and 34 may be configured such that a middle portion of each filament 14 has a second transverse dimension substantially greater than the first transverse dimension.

For some embodiments, the permeable shell 40 may have a first transverse dimension in a collapsed radially constrained state of about 0.2 mm to about 2 mm and a second transverse dimension in a relaxed expanded state of about 4 mm to about 30 mm. For some embodiments, the second transverse dimension of the permeable shell 40 in an expanded state may be about 2 times to about 150 times the first transverse dimension, more specifically, about 10 times to about 25 times the first or constrained transverse dimension. A longitudinal spacing between the proximal end 32 and distal end 34 of the permeable shell 40 in the relaxed expanded state may be about 25% percent to about 75% percent of the spacing between the proximal end 32 and distal end 34 in the constrained cylindrical state. For some embodiments, a major transverse dimension of the permeable shell 40 in a relaxed expanded state may be about 4 mm to about 30 mm, more specifically, about 9 mm to about 15 mm, and even more specifically, about 4 mm to about 8 mm.

Figure 6:
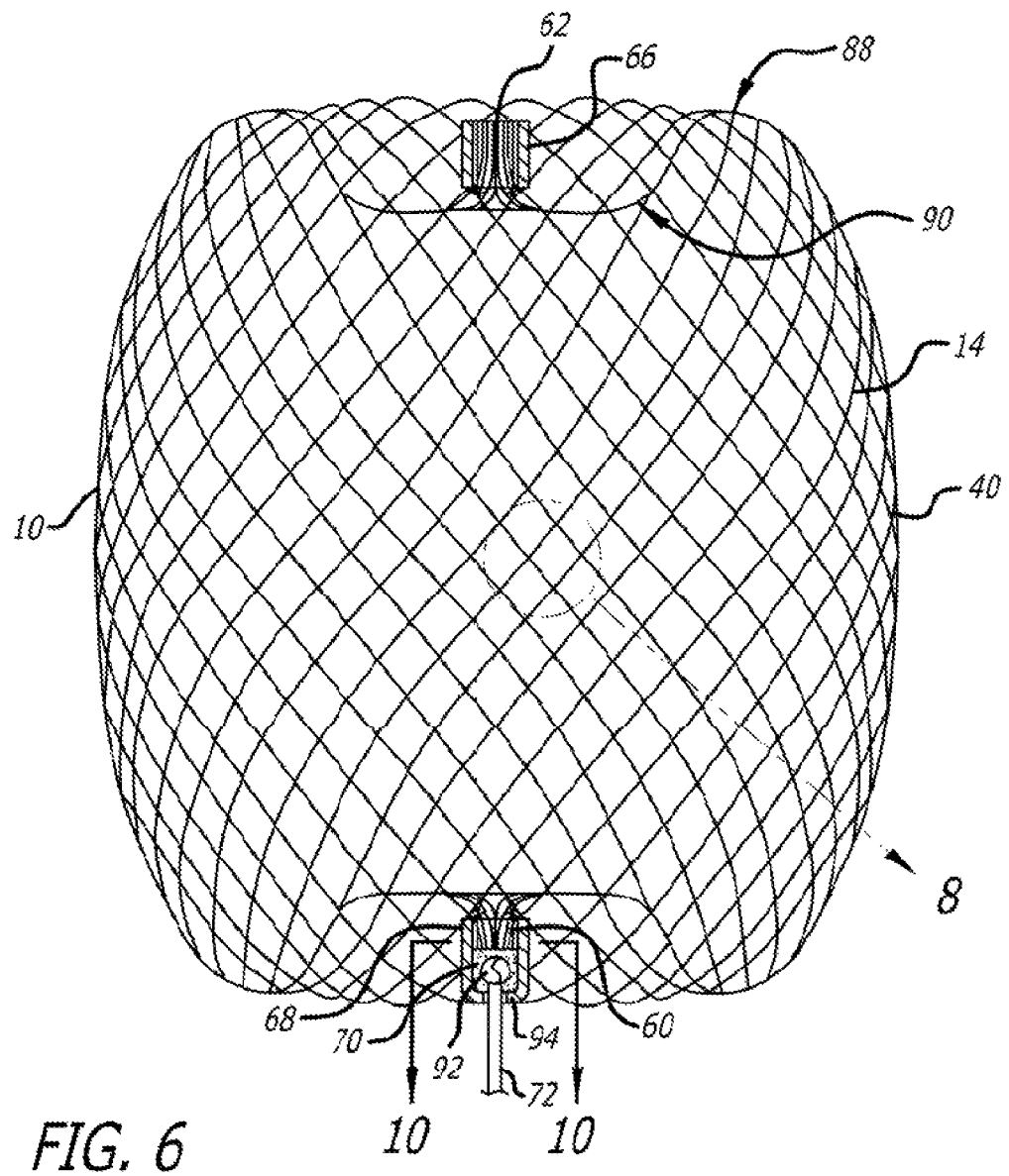
FIG. 6 shows the device of FIG. 4 in longitudinal section taken along lines 6-6 in FIG. 4.

An arced portion of the filaments 14 of the permeable shell 40 may have a sinusoidal-like shape with a first or outer radius 88 and a second or inner radius 90 near the ends of the permeable shell 40 as shown in FIG. 6. This sinusoid-like or multiple curve shape may provide a concavity in the proximal end 32 that may reduce an obstruction of flow in a parent vessel adjacent a vascular defect. For some embodiments, the first radius 88 and second radius 90 of the permeable shell 40 may be between about 0.12 mm to about 3 mm. For some embodiments, the distance between the proximal end 32 and distal end 34 may be less than about 60% of the overall length of the permeable shell 40 for some embodiments. Such a configuration may allow for the distal end 34 to flex downward toward the proximal end 32 when the device 10 meets resistance at the distal end 34 and thus may provide longitudinal conformance. The filaments 14 may be shaped in some embodiments such that there are no portions that are without curvature over a distance of more than about 2 mm. Thus, for some embodiments, each filament 14 may have a substantially continuous curvature. This substantially continuous curvature may provide smooth deployment and may reduce the risk of vessel perforation. For some embodiments, one of the ends 32 or 34 may be retracted or everted to a greater extent than the other so as to be more longitudinally or axially conformal than the other end.

The first radius 88 and second radius 90 of the permeable shell 40 may be between about 0.12 mm to about 3 mm for some embodiments. For some embodiments, the distance between the proximal end 32 and distal end 34 may be more than about 60% of the overall length of the expanded permeable shell 40. Thus, the largest longitudinal distance between the inner surfaces may be about 60% to about 90% of the longitudinal length of the outer surfaces or the overall length of device 10. A gap between the hubs 66 and 68 at the proximal end 32 and distal end 34 may allow for the distal hub 66 to flex downward toward the proximal hub 68 when the device 10 meets resistance at the distal end and thus provides longitudinal conformance. The filaments 14 may be shaped such that there are no portions that are without curvature over a distance of more than about 2 mm. Thus, for some embodiments, each filament 14 may have a substantially continuous curvature. This substantially continuous curvature may provide smooth deployment and may reduce the risk of vessel perforation. The distal end 34 may be retracted or everted to a greater extent than the proximal end 32 such that the distal end portion of the permeable shell 40 may be more radially conformal than the proximal end portion. Conformability of a distal end portion may provide better device conformance to irregular shaped aneurysms or other vascular defects. A convex surface of the device may flex inward forming a concave surface to conform to curvature of a vascular site.

Figure 10:
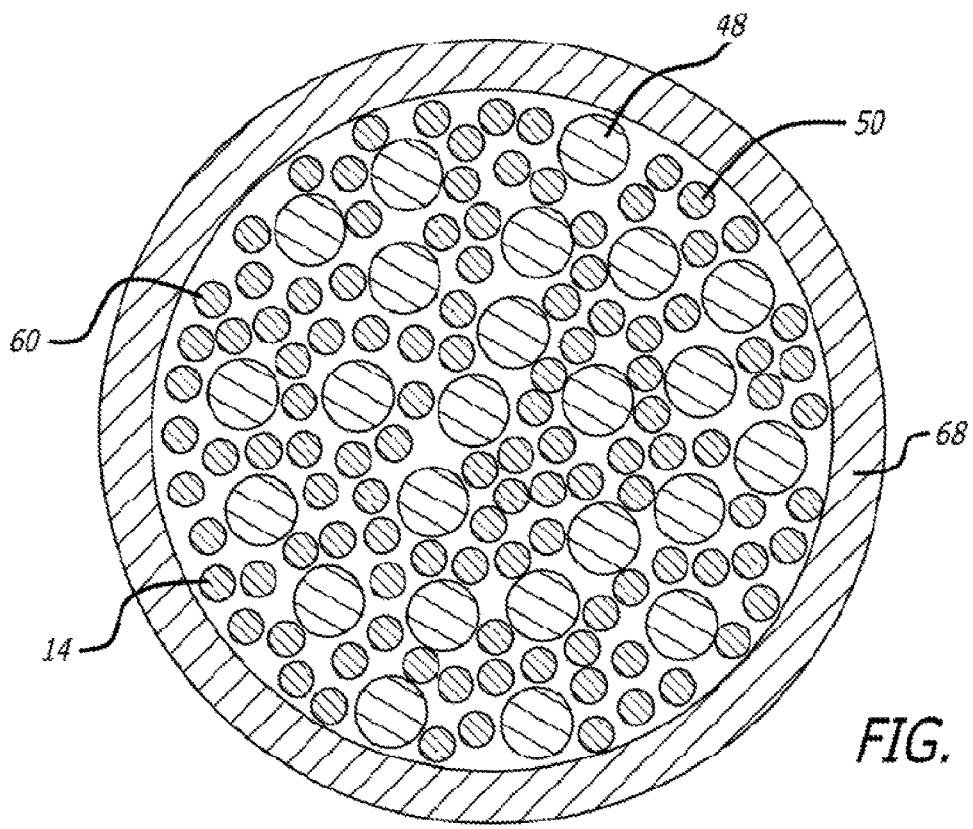
FIG. 10 is a transverse sectional view of a proximal hub portion of the device in FIG. 6 indicated by lines 10-10 in FIG. 6.
Figure 11:
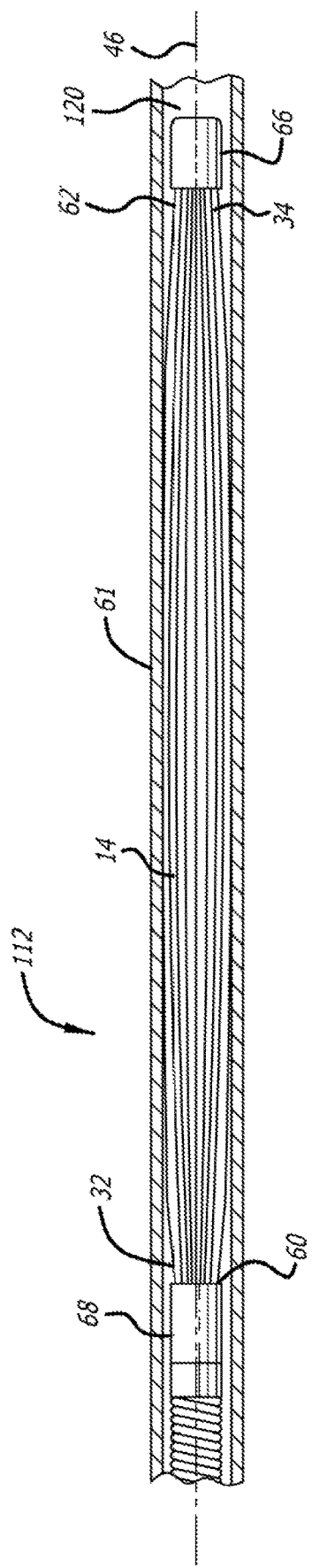
FIG. 11 is an elevation view in partial section of a distal end of a delivery catheter with the device for treatment of a patient's vasculature of FIG. 3 disposed therein in a collapsed constrained state.

FIG. 10 shows an enlarged view of the filaments 14 disposed within a proximal hub 68 of the device 10 with the filaments 14 of two different sizes constrained and tightly packed by an outer ring of the proximal hub 68. The tether member 72 may optionally be disposed within a middle portion of the filaments 14 or within the cavity 70 of the proximal hub 68 proximal of the proximal ends 60 of the filaments 14 as shown in FIG. 6. The distal end of the tether 72 may be secured with a knot 92 formed in the distal end thereof which is mechanically captured in the cavity 70 of the proximal hub 68 formed by a proximal shoulder portion 94 of the proximal hub 68. The knotted distal end 92 of the tether 72 may also be secured by bonding or potting of the distal end of the tether 72 within the cavity 70 and optionally amongst the proximal ends 60 of the filaments 14 with mechanical compression, adhesive bonding, welding, soldering, brazing or the like. The tether embodiment 72 shown in FIG. 6 has a knotted distal end 92 potted in the cavity of the proximal hub 68 with an adhesive. Such a tether 72 may be a dissolvable, severable or releasable tether that may be part of a delivery apparatus 111 used to deploy the device 10 as shown in FIG. 11 and FIGS. 23-26. FIG. 10 also shows the large filaments 48 and small filaments 50 disposed within and constrained by the proximal hub 68 which may be configured to secure the large and small filaments 48 and 50 in place relative to each other within the outer ring of the proximal hub 68.

Figure 7:
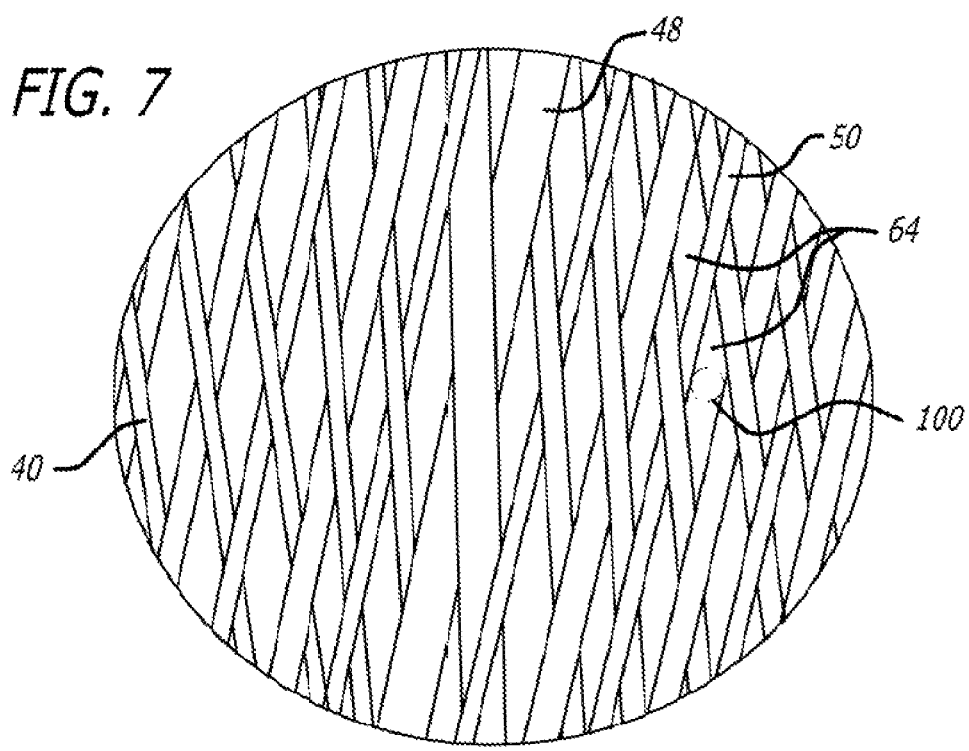
FIG. 7 is an enlarged view of the woven filament structure taken from the encircled portion 7 shown in FIG. 5.
Figure 8:
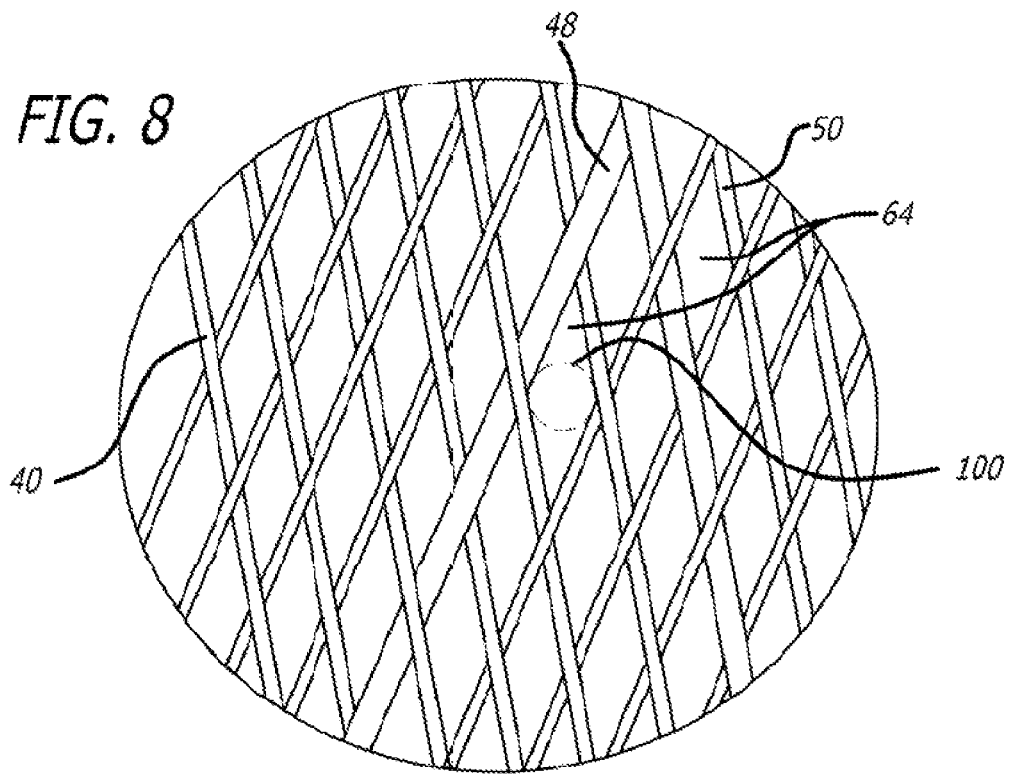
FIG. 8 is an enlarged view of the woven filament structure taken from the encircled portion 8 shown in FIG. 6.
Figure 9:
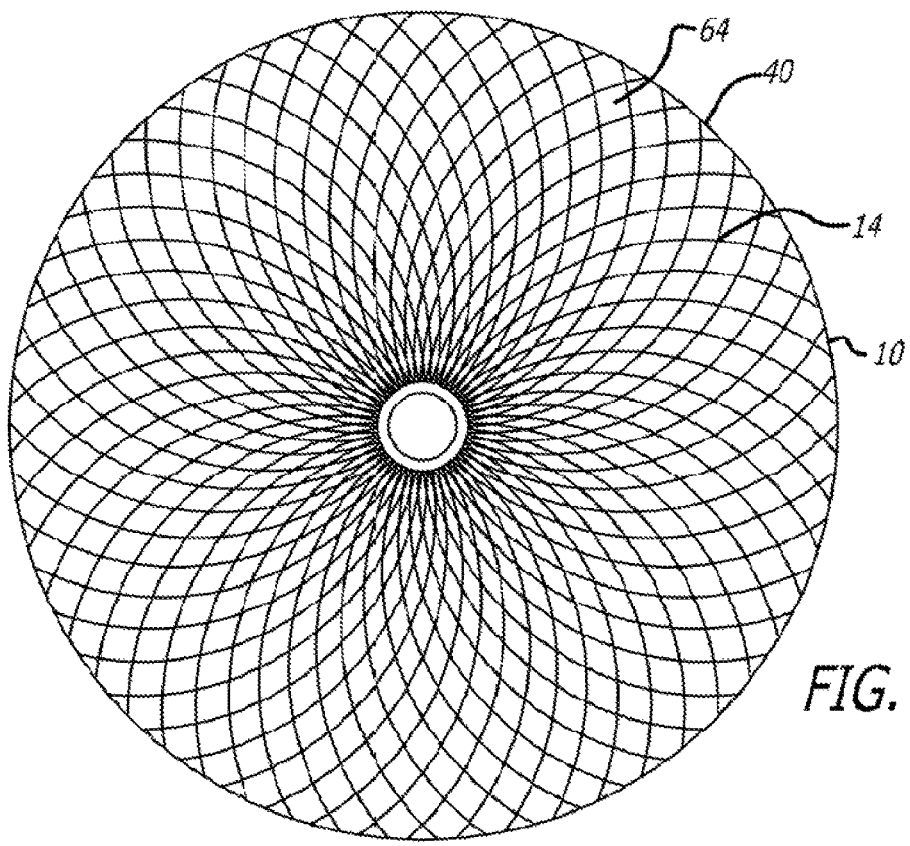
FIG. 9 is a proximal end view of the device of FIG. 3.

FIGS. 7 and 8 illustrate some configuration embodiments of braided filaments 14 of a permeable shell 40 of the device 10 for treatment of a patient's vasculature. The braid structure in each embodiment is shown with a circular shape 100 disposed within a pore 64 of a woven or braided structure with the circular shape 100 making contact with each adjacent filament segment. The pore opening size may be determined at least in part by the size of the filament elements 14 of the braid, the angle overlapping filaments make relative to each other and the picks per inch of the braid structure. For some embodiments, the cells or openings 64 may have an elongated substantially diamond shape as shown in FIG. 7, and the pores or openings 64 of the permeable shell 40 may have a substantially more square shape toward a middle portion 30 of the device 10, as shown in FIG. 8. The diamond shaped pores or openings 64 may have a length substantially greater than the width particularly near the hubs 66 and 68. In some embodiments, the ratio of diamond shaped pore or opening length to width may exceed a ratio of 3 to 1 for some cells. The diamond-shaped openings 64 may have lengths greater than the width thus having an aspect ratio, defined as Length/Width of greater than 1. The openings 64 near the hubs 66 and 68 may have substantially larger aspect ratios than those farther from the hubs as shown in FIG. 7. The aspect ratio of openings 64 adjacent the hubs may be greater than about 4 to 1. The aspect ratio of openings 64 near the largest diameter may be between about 0.75 to 1 and about 2 to 1 for some embodiments. For some embodiments, the aspect ratio of the openings 64 in the permeable shell 40 may be about 0.5 to 1 to about 2 to 1.

The pore size defined by the largest circular shapes 100 that may be disposed within openings 64 of the braided structure of the permeable shell 40 without displacing or distorting the filaments 14 surrounding the opening 64 may range in size from about 0.005 inches to about 0.01 inches, more specifically, about 0.006 inches to about 0.009 inches, even more specifically, about 0.007 inches to about 0.008 inches for some embodiments. In addition, at least some of the openings 64 formed between adjacent filaments 14 of the permeable shell 40 of the device 10 may be configured to allow blood flow through the openings 64 only at a velocity below a thrombotic threshold velocity. For some embodiments, the largest openings 64 in the permeable shell structure 40 may be configured to allow blood flow through the openings 64 only at a velocity below a thrombotic threshold velocity. As discussed above, the pore size may be less than about 0.016 inches, more specifically, less than about 0.012 inches for some embodiments. For some embodiments, the openings 64 formed between adjacent filaments 14 may be about 0.005 inches to about 0.04 inches.

Figure 12:
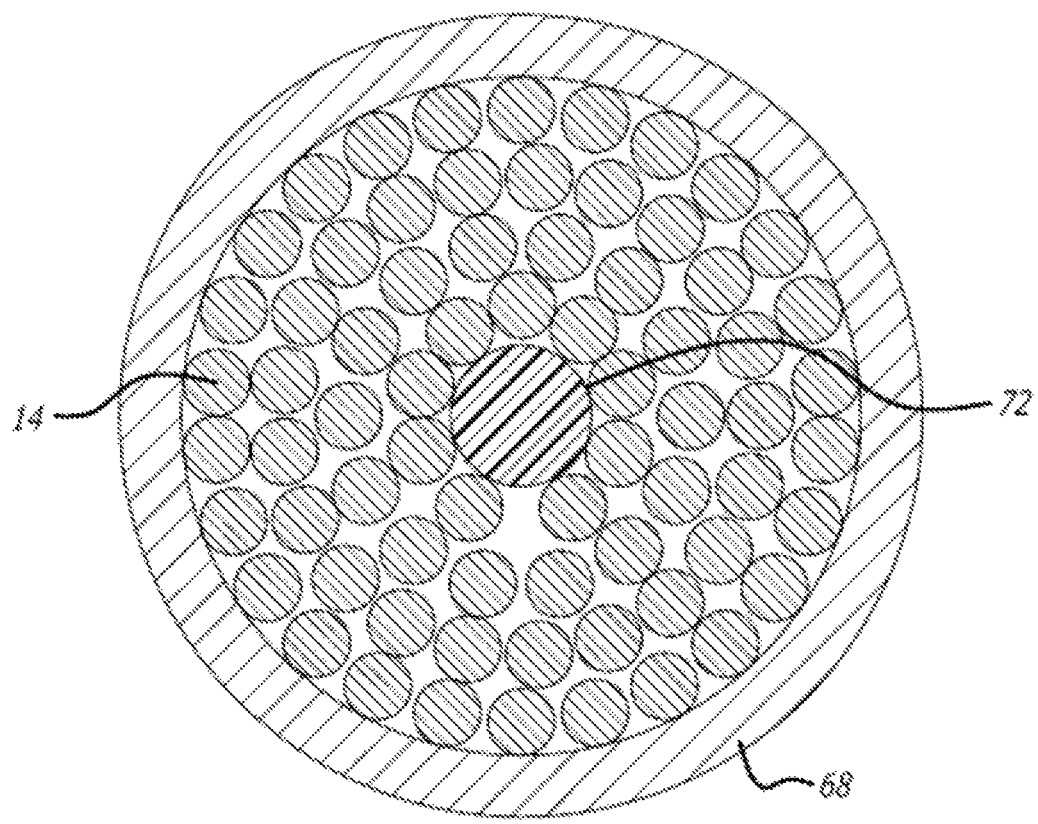
FIG. 12 illustrates an embodiment of a filament configuration for a device for treatment of a patient's vasculature.

FIG. 12 illustrates in transverse cross section an embodiment of a proximal hub 68 showing the configuration of filaments which may be tightly packed and radially constrained by an inside surface of the proximal hub 68. In some embodiments, the braided or woven structure of the permeable shell 40 formed from such filaments 14 may be constructed using a large number of small filaments. The number of filaments 14 may be greater than 125 and may also be between about 80 filaments and about 180 filaments. As discussed above, the total number of filaments 14 for some embodiments may be about 70 filaments to about 300 filaments, more specifically, about 100 filaments to about 200 filaments. In some embodiments, the braided structure of the permeable shell 40 may be constructed with two or more sizes of filaments 14. For example, the structure may have several larger filaments that provide structural support and several smaller filaments that provide the desired pore size and density and thus flow resistance to achieve a thrombotic threshold velocity in some cases. For some embodiments, small filaments 50 of the permeable shell 40 may have a transverse dimension or diameter of about 0.0006 inches to about 0.002 inches for some embodiments and about 0.0004 inches to about 0.001 inches in other embodiments. The large filaments 48 may have a transverse dimension or diameter of about 0.0015 inches to about 0.004 inches in some embodiments and about 0.001 inches to about 0.004 inches in other embodiments. The filaments 14 may be braided in a plain weave that is one under, one over structure (shown in FIGS. 7 and 8) or a supplementary weave; more than one warp interlace with one or more than one weft. The pick count may be varied between about 25 and 200 picks per inch (PPI).

In order to treat large and giant aneurysms, occlusive devices characterized by multiple permeable shells connected by embolic coils may have strong application.

Figure 13:
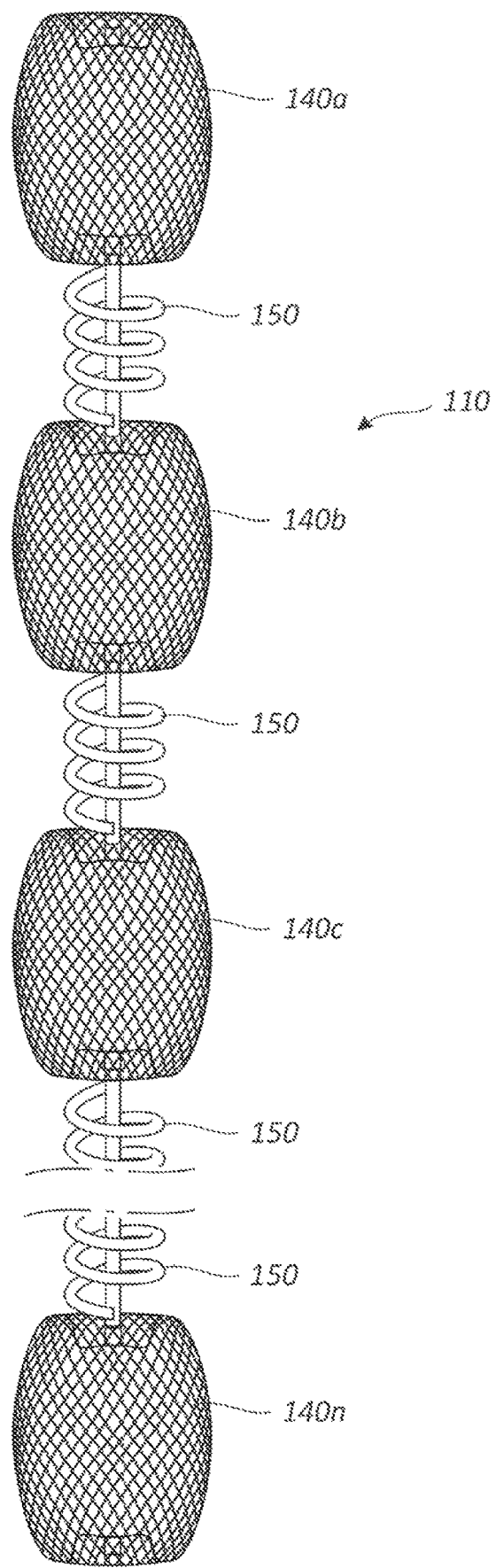
FIG. 13 illustrates an embodiment of a device with multiple permeable shells.

FIG. 13 depicts an intrasaccular device that includes multiple permeable shells coupled together with helical coils. The device 110 includes at least two or more, alternatively three or more, alternatively at least four or more, alternatively at least five or more self-expanding resilient permeable shells 140a-n, each having a proximal end, a distal end, a longitudinal axis, and further comprising a plurality of elongate resilient filaments. The filaments have a woven structure and are secured relative to each other at the proximal ends and distal ends of each of the permeable shells 140a-n. The permeable shells 140a-n of the device 110 each has a radially constrained elongated state configured for delivery within a microcatheter, with the thin woven filaments extending longitudinally from the proximal end to the distal end of each permeable shell radially adjacent each other along a length of the filaments. The permeable shells 140a-n each have an expanded relaxed state with a globular and longitudinally shortened configuration relative to the radially constrained state. In the expanded state, the woven filaments form the self-expanding resilient permeable shell 140a-b in a smooth path radially expanded from a longitudinal axis of the permeable shell between the proximal end and distal end. The expanded state of the permeable shells 140a-n can have a diameter of about 4 mm, alternatively about 5 mm, alternatively about 6 mm, alternatively about 7 mm, alternatively about 8 mm, alternatively about 9 mm, alternatively about 10 mm, alternatively about 11 mm. The expanded state of the permeable shells can have a height or length of about 2.6 mm, about 3 mm, about 3.6 mm, about 4 mm, about 4.6 mm, about 5 mm, about 5.6 mm, about 6 mm, about 6.6 mm, about 7 mm, about 7.6 mm, about 8 mm, about 8.6 mm, about 9 mm, about 9.6 mm, or about 10 mm. The woven structure of the filaments forming the permeable shells 140a-n includes a plurality of openings in the permeable shell 40 formed between the woven filaments. Intrasaccular occlusive devices that include a permeable shell formed from a woven or braided mesh have been described in US 2017/0095254, US 2016/0249934, US 2016/0367260, US 2016/0249937, US 2018/0000489, and 2018/0206849, all of which are hereby expressly incorporated by reference in their entirety for all purposes. As described with respect to other embodiments of permeable shells, the filaments may be made from metals and metal alloys such as nitinol, platinum, tungsten, nickel, and combinations thereof. All or a portion of the filaments may also be composite filaments, such as drawn filled tubes (DFT), as described in US 2016/0249934, which was previously incorporated by reference in its entirety for all purposes. The DFT may include a highly radiopaque core inside a tubing. For instance, the DFT may include a platinum core inside of a nitinol tubing.

The multiple permeable shells may be interlinked using helical coils 150. Helical coils 50 having different lengths and diameters can be used to leverage deliverability as well as improve packing of the aneurysm. Helical coils 150 may have an internal diameter (ID) of about 2 mm, about 3 mm, about 4 mm, about 5 mm, about 6 mm, about 7 mm, about 8 mm, or about 10 mm. Alternatively, the helical coils 50 may have IDs between about 2 and about 24 mm, alternatively between about 2 and about 20 mm, alternatively between about 2 and about 16 mm, alternatively between about 2 and about 12 mm, alternatively between about 2 and about 8 mm, alternatively between about 2 and about 6 mm. The length of the helical coils may be approx. 2-68 cm, alternatively 2-43 cm, alternatively 6-20 cm.

In some embodiments, the helical coils 150 may include hydrogel. Hydrogels are compounds that absorb water from the blood and surrounding tissue and swell in response—thereby increasing their occlusive effect. In some examples, the coils 150 utilize an inert hydrogel core—for instance, the hydrogel may be affixed internally along one more wound segments of the coil. Alternatively, the hydrogel may be coated on an external surface of the wound wire comprising the coil 150. A detailed description of coils, including hydrogel coils, can be found in U.S. Pat. Nos. 6,238,403, 6,878,384, 8,377,091, and 10,499,925, which are hereby expressly incorporated by reference in their entirety for all purposes.

The overall shape of the device may be delivered as a helix. The device 110 may include between about 3 and 12, alternatively between about 4 and 10, alternatively between about 5 and 9, alternatively between about 5 and 8 permeable shells. The permeable shells of the device 110 may have the same or different expanded diameters and the same or different heights. For example, a device 110 may have between about 5 and about 9 permeable shells, all having an expanded diameter of about 7 mm that are coupled together using 4×8 mm helical coils 50. Alternatively, the permeable shells 140a-n of device 110 may have different diameters. For example, the distal most permeable shell 140a-n may have the smallest diameter of the permeable shells (e.g., 3-5 mm diameter) in the device 110 and the proximal most permeable shell may have the largest diameter of the permeable shells (e.g., 9-11 mm) in the device 110 to provide maximum coverage at the neck of the aneurysm. The distal most permeable shell would sit near the dome of the aneurysm, while the proximal most shell would sit near the neck of the aneurysm.

In some embodiments, the most proximal permeable shell 140a-n that sits along the implant device 110 can be sized and configured to sit directly at the neck of the aneurysm—so as to seal the aneurysm and prevent the rest of the device 110 from falling out of the aneurysm. In this way, these embodiments can be configured such that normal accessory devices (such as stents or balloons that typically have to be deployed adjacent the neck region of the aneurysm to prevent embolic coils from falling out of the aneurysm) can be avoided.

Similarly, the coils 150 may have the same or different lengths and the same or different internal diameters. For example, the coils 150 used to couple the permeable shells at the distal end of the device 110 can may have a diameter of about 1.5 mm to about 3 mm diameter, alternatively about 1.0 mm to about 3.5 mm diameter, alternatively about 1.0 mm to about 2.5 mm diameter, alternatively about 0.75 mm to about 2.5 mm diameter, alternatively about 1.0 mm to about 3.0 mm diameter, and the coils used to couple the permeable shells at the proximal end of the device 110 can have a diameter of about 3 mm to about 6 mm, alternatively about 2.5 mm to about 6.5 mm diameter, alternatively about 3.0 mm to about 5.5 mm diameter, alternatively about 3.5 mm to about 5.5 mm diameter, alternatively about 3.5 mm to about 5.0 mm diameter, alternatively about 3.0 mm to about 5.0 mm diameter, alternatively about 2.5 mm to about 4.5 mm diameter. The length for coils 150 can vary between about 3 cm to about 15 cm, alternatively between about 4 cm to about 15 cm, alternatively between about 4 cm to about 12 cm, alternatively between about 5 cm to about 12 cm, alternatively between about 5 cm to about 10 cm, alternatively between about 6 cm to about 12 cm, alternatively between about 7 cm to about 12 cm. The coils 150 connecting the permeable shells at the distal end of the device, (e.g., connecting the 2, alternatively 3, alternatively 4 distal-most permeable shells) may have a smaller diameter than the permeable shells at the proximal end of the device (e.g., connecting the 2, alternatively 3, alternatively 4 proximal-most permeable shells). The helical coils 50 may be attached between the proximal and distal ends of adjacent permeable shells, i.e., the coil could be attached to the proximal marker band of a distal permeable shell and the distal marker band of a proximal permeable shell. A total length of the device, including the plurality of permeable shells and the coils connecting adjacent permeable shells, may be less than about 120 cm, alternatively less than about 110 cm, alternatively less than about 100 cm, alternatively less than about 90 cm, alternatively less than about 80 cm, alternatively less than about 70 cm, alternatively between about 30 cm and about 110 cm, alternatively between about 40 cm and about 100 cm, alternatively between about 50 cm and about 100 cm, alternatively between about 60 cm and about 100 cm, alternatively between about 70 cm and about 100 cm. In some embodiments, the coils may not extend through the interior of the permeable shells. Thus, in some embodiments, the interior cavities of the permeable shells are empty and do not contain any portion of the coils 150.

The device 110 may be attached to a delivery pusher. The proximal marker band of the proximal most permeable shell may be attached to the distal end of the delivery pusher. The device may be delivered through a microcatheter, e.g., a catheter with an inner delivery lumen sized between about 0.017 inches and about 0.027 inches, to ensure a smooth, low profile delivery. Delivery can be accomplished as described in other publications, which have been expressly incorporated by reference in their entirety, and also as described below.

For some embodiments, the permeable shell 40, 140 or portions thereof may be porous and may be highly permeable to liquids. In contrast to most vascular prosthesis fabrics or grafts which typically have a water permeability below 2,000 ml/min/cm$^2$ when measured at a pressure of 120 mmHg, the permeable shell 40 of some embodiments discussed herein may have a water permeability greater than about 2,000 ml/min/cm$^2$, in some cases greater than about 2,500 ml/min/cm$^2$. For some embodiments, water permeability of the permeable shell 40 or portions thereof may be between about 2,000 and 10,000 ml/min/cm$^2$, more specifically, about 2,000 ml/min/cm$^2$ to about 15,000 ml/min/cm$^2$, when measured at a pressure of 120 mmHg.

Device embodiments and components thereof may include metals, polymers, biologic materials and composites thereof. Suitable metals include zirconium-based alloys, cobalt-chrome alloys, nickel-titanium alloys, platinum, tantalum, stainless steel, titanium, gold, and tungsten. Potentially suitable polymers include but are not limited to acrylics, silk, silicones, polyvinyl alcohol, polypropylene, polyvinyl alcohol, polyesters (e.g., polyethylene terephthalate or PET), PolyEtherEther Ketone (PEEK), polytetrafluoroethylene (PTFE), polycarbonate urethane (PCU) and polyurethane (PU). Device embodiments may include a material that degrades or is absorbed or eroded by the body. A bioresorbable (e.g., breaks down and is absorbed by a cell, tissue, or other mechanism within the body) or bioabsorbable (similar to bioresorbable) material may be used. Alternatively, a bioerodable_(e.g., erodes or degrades over time by contact with surrounding tissue fluids, through cellular activity or other physiological degradation mechanisms), biodegradable (e.g., degrades over time by enzymatic or hydrolytic action, or other mechanism in the body), or dissolvable material may be employed. Each of these terms is interpreted to be interchangeable. bioabsorbable polymer. Potentially suitable bioabsorbable materials include polylactic acid (PLA), poly(alpha-hydroxy acid) such as poly-L-lactide (PLLA), poly-D-lactide (PDLA), polyglycolide (PGA), polydioxanone, polycaprolactone, polygluconate, polylactic acid-polyethylene oxide copolymers, modified cellulose, collagen, poly(hydroxybutyrate), polyanhydride, polyphosphoester, poly(amino acids), or related copolymer materials. An absorbable composite fiber may be made by combining a reinforcement fiber made from a copolymer of about 18% glycolic acid and about 82% lactic acid with a matrix material consisting of a blend of the above copolymer with about 20% polycaprolactone (PCL).

Permeable shell embodiments 40, 140 may be formed at least in part of wire, ribbon, or other filamentary elements 14, 114. These filamentary elements 14 may have circular, elliptical, ovoid, square, rectangular, or triangular cross-sections. Permeable shell embodiments 40 may also be formed using conventional machining, laser cutting, electrical discharge machining (EDM) or photochemical machining (PCM). If made of a metal, it may be formed from either metallic tubes or sheet material.

Figure 17:
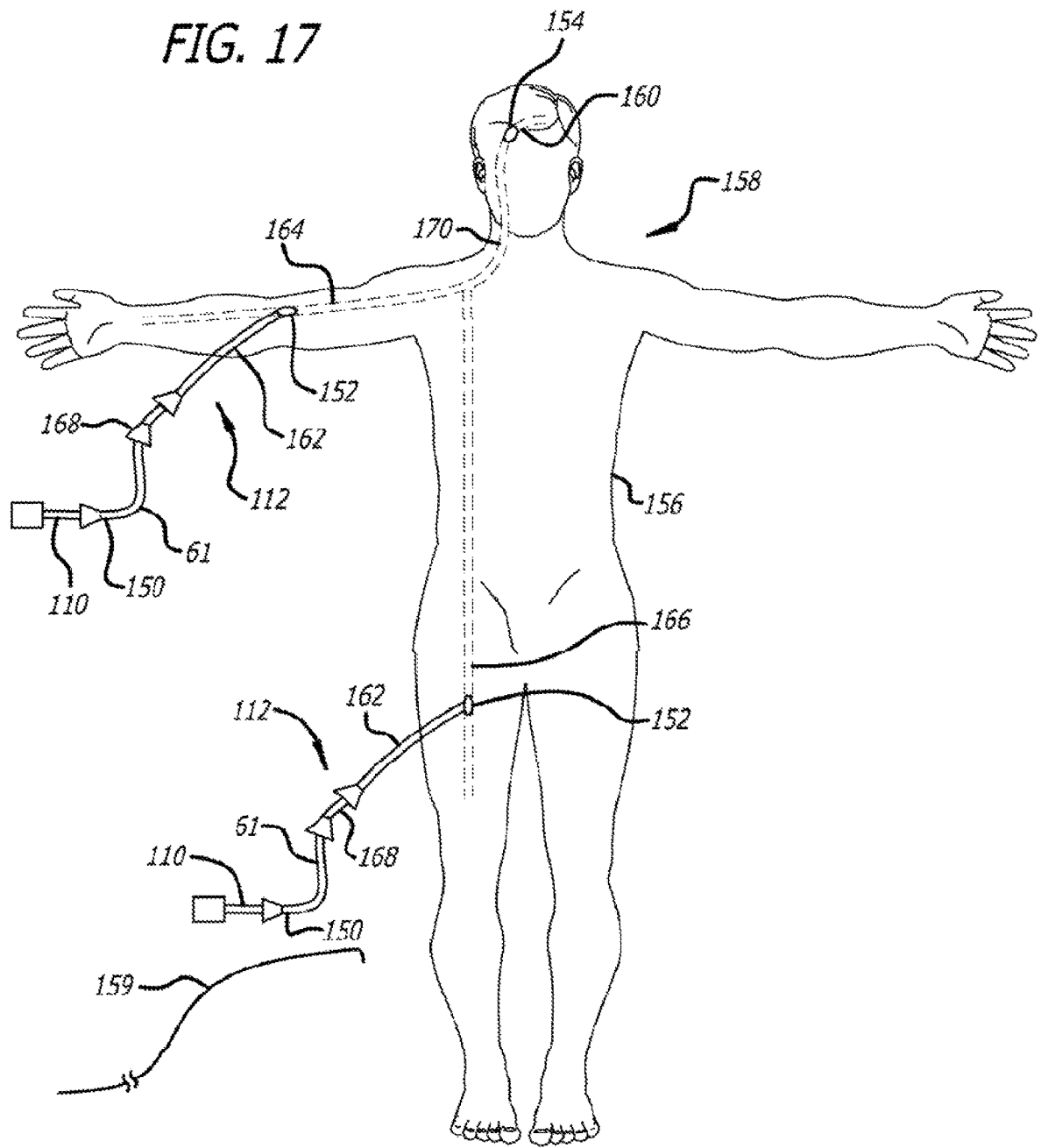
FIG. 17 is a schematic view of a patient being accessed by an introducer sheath, a microcatheter and a device for treatment of a patient's vasculature releasably secured to a distal end of a delivery device or actuator.
Figure 18:
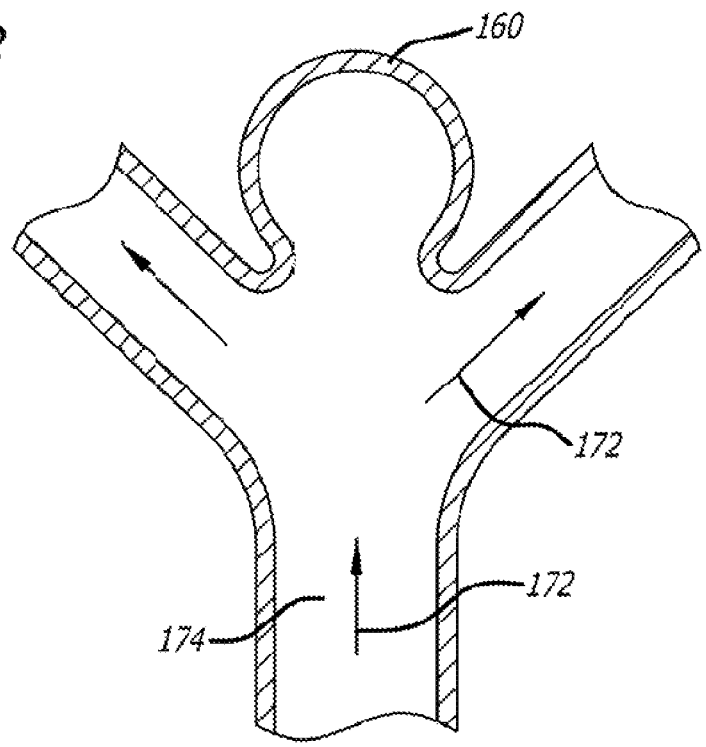
FIG. 18 is a sectional view of a terminal aneurysm.

Device embodiments 10, 110 discussed herein may be delivered and deployed from a delivery and positioning system 112 that includes a microcatheter 61, such as the type of microcatheter 61 that is known in the art of neurovascular navigation and therapy. Device embodiments for treatment of a patient's vasculature 10, 110 may be elastically collapsed and restrained by a tube or other radial restraint, such as an inner lumen 120 of a microcatheter 61, for delivery and deployment. The microcatheter 61 may generally be inserted through a small incision 152 accessing a peripheral blood vessel such as the femoral artery or brachial artery. The microcatheter 61 may be delivered or otherwise navigated to a desired treatment site 154 from a position outside the patient's body 156 over a guidewire 159 under fluoroscopy or by other suitable guiding methods. The guidewire 159 may be removed during such a procedure to allow insertion of the device 10, 110 secured to a delivery apparatus 111 of the delivery system 112 through the inner lumen 120 of a microcatheter 61 in some cases. FIG. 17 illustrates a schematic view of a patient 158 undergoing treatment of a vascular defect 160 as shown in FIG. 18. An access sheath 162 is shown disposed within either a radial artery 164 or femoral artery 166 of the patient 158 with a delivery system 112 that includes a microcatheter 61 and delivery apparatus 111 disposed within the access sheath 162. The delivery system 112 is shown extending distally into the vasculature of the patient's brain adjacent a vascular defect 160 in the patient's brain.

Access to a variety of blood vessels of a patient may be established, including arteries such as the femoral artery 166, radial artery 164, and the like in order to achieve percutaneous access to a vascular defect 160. In general, the patient 158 may be prepared for surgery and the access artery is exposed via a small surgical incision 152 and access to the lumen is gained using the Seldinger technique where an introducing needle is used to place a wire over which a dilator or series of dilators dilates a vessel allowing an introducer sheath 162 to be inserted into the vessel. This would allow the device to be used percutaneously. With an introducer sheath 162 in place, a guiding catheter 168 is then used to provide a safe passageway from the entry site to a region near the target site 154 to be treated. For example, in treating a site in the human brain, a guiding catheter 168 would be chosen which would extend from the entry site 152 at the femoral artery up through the large arteries extending around the heart through the aortic arch, and downstream through one of the arteries extending from the upper side of the aorta such as the carotid artery 170. Typically, a guidewire 159 and neurovascular microcatheter 61 are then placed through the guiding catheter 168 and advanced through the patient's vasculature, until a distal end 151 of the microcatheter 61 is disposed adjacent or within the target vascular defect 160, such as an aneurysm. Exemplary guidewires 159 for neurovascular use include the Synchro2® made by Boston Scientific and the Glidewire Gold Neuro® made by MicroVention Terumo. Typical guidewire sizes may include 0.014 inches and 0.018 inches. Once the distal end 151 of the catheter 61 is positioned at the site, often by locating its distal end through the use of radiopaque marker material and fluoroscopy, the catheter is cleared. For example, if a guidewire 159 has been used to position the microcatheter 61, it is withdrawn from the catheter 61 and then the implant delivery apparatus 111 is advanced through the microcatheter 61.

Delivery and deployment of device embodiments 10, 110 discussed herein may be carried out by first compressing the device 10, 110 to a radially constrained and longitudinally flexible state as shown in FIG. 11. The device 10, 110 may then be delivered to a desired treatment site 154 while disposed within the microcatheter 61, and then ejected or otherwise deployed from a distal end 151 of the microcatheter 61. In other method embodiments, the microcatheter 61 may first be navigated to a desired treatment site 154 over a guidewire 159 or by other suitable navigation techniques. The distal end of the microcatheter 61 may be positioned such that a distal port of the microcatheter 61 is directed towards or disposed within a vascular defect 160 to be treated and the guidewire 159 withdrawn. The device 10, 110 secured to a suitable delivery apparatus 111 may then be radially constrained, inserted into a proximal portion of the inner lumen 120 of the microcatheter 61 and distally advanced to the vascular defect 160 through the inner lumen 120.

Once disposed within the vascular defect 160, the device 10, 110 may then allowed to assume an expanded relaxed or partially relaxed state with the permeable shell 40, 140 of the device spanning or partially spanning a portion of the vascular defect 160 or the entire vascular defect 160. The device 10, 110 may also be activated by the application of an energy source to assume an expanded deployed configuration once ejected from the distal section of the microcatheter 61 for some embodiments. Once the device 10 is deployed at a desired treatment site 154, the microcatheter 61 may then be withdrawn.

Figure 19:
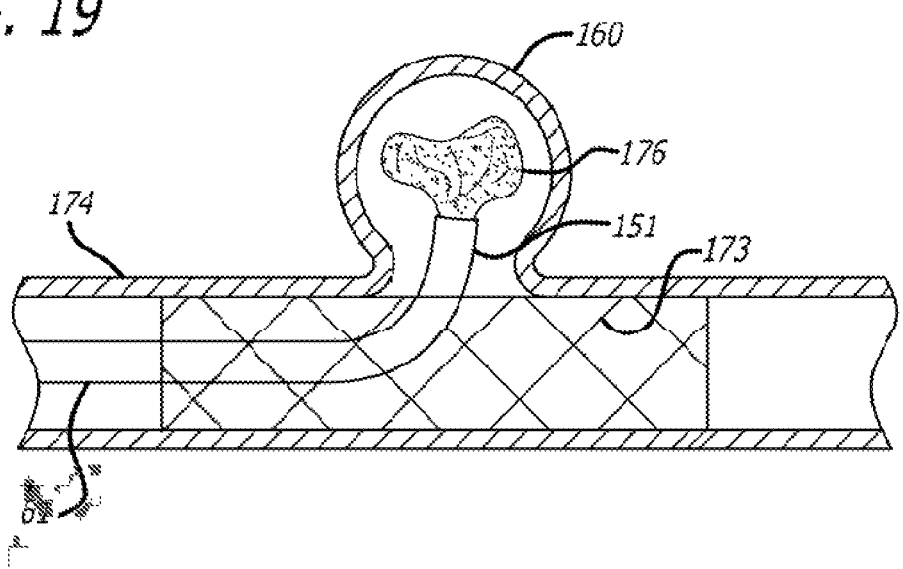
FIG. 19 is a sectional view of an aneurysm.

Some embodiments of devices for the treatment of a patient's vasculature 10, 110 discussed herein may be directed to the treatment of specific types of defects of a patient's vasculature. For example, referring to FIG. 18, an aneurysm 160 commonly referred to as a terminal aneurysm is shown in section. Terminal aneurysms occur typically at bifurcations in a patient's vasculature where blood flow, indicated by the arrows 172, from a supply vessel splits into two or more branch vessels directed away from each other. The main flow of blood from the supply vessel 174, such as a basilar artery, sometimes impinges on the vessel where the vessel diverges and where the aneurysm sack forms. Terminal aneurysms may have a well defined neck structure where the profile of the aneurysm 160 narrows adjacent the nominal vessel profile, but other terminal aneurysm embodiments may have a less defined neck structure or no neck structure. FIG. 19 illustrates a typical berry type aneurysm 160 in section where a portion of a wall of a nominal vessel section weakens and expands into a sack like structure ballooning away from the nominal vessel surface and profile. Some berry type aneurysms may have a well defined neck structure as shown in FIG. 19, but others may have a less defined neck structure or none at all. FIG. 19 also shows some optional procedures wherein a stent 173 or other type of support has been deployed in the parent vessel 174 adjacent the aneurysm. Also, shown is embolic material 176 being deposited into the aneurysm 160 through a microcatheter 61. Either or both of the stent 173 and embolic material 176 may be so deployed either before or after the deployment of a device for treatment of a patient's vasculature 10.

Figure 28:
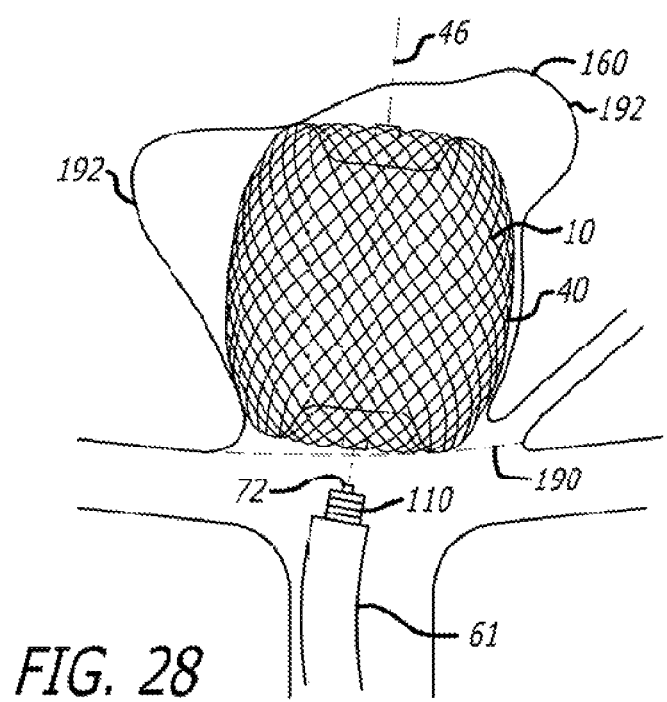
FIG. 28 is an elevation view in partial section of an embodiment of a device for treatment of a patient's vasculature deployed within an irregularly shaped aneurysm.

Prior to delivery and deployment of a device for treatment of a patient's vasculature 10, 110, it may be desirable for the treating physician to choose an appropriately sized device 10, 110 to optimize the treatment results. Some embodiments of treatment may include estimating a volume of a vascular site or defect 160 to be treated and selecting a device 10, 110 with a volume that is substantially the same volume or slightly over-sized relative to the volume of the vascular site or defect 160. The volume of the vascular defect 160 to be occluded may be determined using three-dimensional angiography or other similar imaging techniques along with software which calculates the volume of a selected region. The amount of over-sizing may be between about 2% and 15% of the measured volume. In some embodiments, such as a very irregular shaped aneurysm, it may be desirable to under-size the volume of the device 10, 110. Small lobes or "daughter aneurysms" may be excluded from the volume, defining a truncated volume which may be only partially filled by the device without affecting the outcome. A device 10, 110 deployed within such an irregularly shaped aneurysm 160 is shown in FIG. 28 discussed below. Such a method embodiment may also include implanting or deploying the device 10, 110 so that the vascular defect 160 is substantially filled volumetrically by a combination of device and blood contained therein. The device 10, 110 may be configured to be sufficiently conformal to adapt to irregular shaped vascular defects 160 so that at least about 75%, in some cases about 80%, of the vascular defect volume is occluded by a combination of device 10, 110 and blood contained therein.

Figure 20:
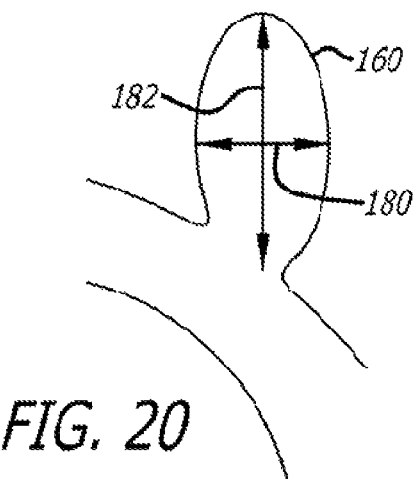
FIG. 20 is a schematic view in section of an aneurysm showing perpendicular arrows which indicate interior nominal longitudinal and transverse dimensions of the aneurysm.
Figure 21:
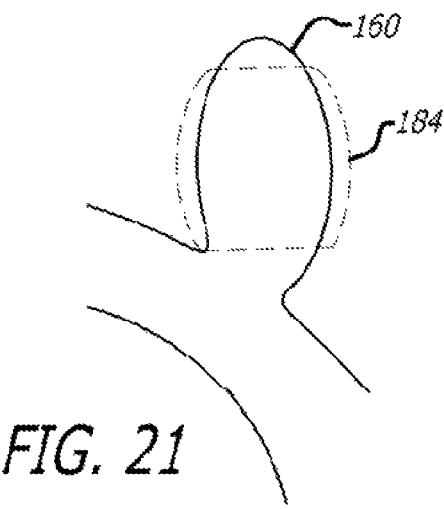
FIG. 21 is a schematic view in section of the aneurysm of FIG. 20 with a dashed outline of a device for treatment of a patient's vasculature in a relaxed unconstrained state that extends transversely outside of the walls of the aneurysm.
Figure 22:
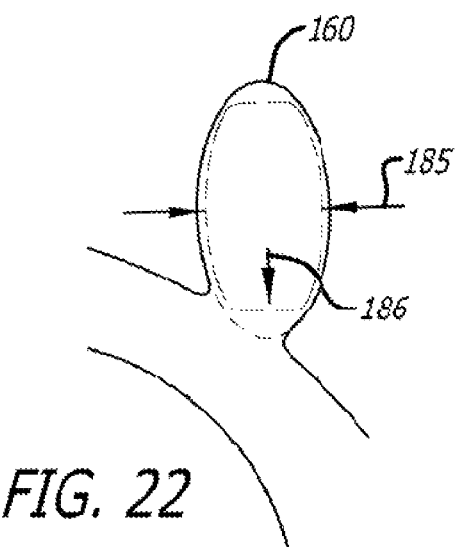
FIG. 22 is a schematic view in section of an outline of a device represented by the dashed line in FIG. 21 in a deployed and partially constrained state within the aneurysm.

In particular, for some treatment embodiments, it may be desirable to choose a device 10, 110 that is properly oversized in a transverse dimension so as to achieve a desired conformance, radial force and fit after deployment of the device 10. FIGS. 20-22 illustrate a schematic representation of how a device 10, 110 may be chosen for a proper fit after deployment that is initially oversized in a transverse dimension by at least about 10% of the largest transverse dimension of the vascular defect 160 and sometimes up to about 100% of the largest transverse dimension. For some embodiments, the device 10, 110 may be oversized a small amount (e.g., less than about 1.5 mm) in relation to measured dimensions for the width, height or neck diameter of the vascular defect 160.

In FIG. 20, a vascular defect 160 in the form of a cerebral aneurysm is shown with horizontal arrows 180 and vertical arrows 182 indicating the approximate largest interior dimensions of the defect 160. Arrow 180 extending horizontally indicates the largest transverse dimension of the defect 160. In FIG. 21, a dashed outline 184 of a device for treatment of the vascular defect is shown superimposed over the vascular defect 160 of FIG. 20 illustrating how a device 10, 110 that has been chosen to be approximately 20% oversized in a transverse dimension would look in its unconstrained, relaxed state. FIG. 22 illustrates how the device 10, 110, which is indicated by the dashed line 184 of FIG. 21 might conform to the interior surface of the vascular defect 160 after deployment whereby the nominal transverse dimension of the device 10, 110 in a relaxed unconstrained state has now been slightly constrained by the inward radial force 185 exerted by the vascular defect 160 on the device 10, 110. In response, as the filaments 14, 114 of the device 10, 110 and thus the permeable shell 40, 140 made therefrom have a constant length, the device 10, 110 has assumed a slightly elongated shape in the axial or longitudinal axis of the device 10 so as to elongate and better fill the interior volume of the defect 160 as indicated by the downward arrow 186 in FIG. 22.

Figure 23:
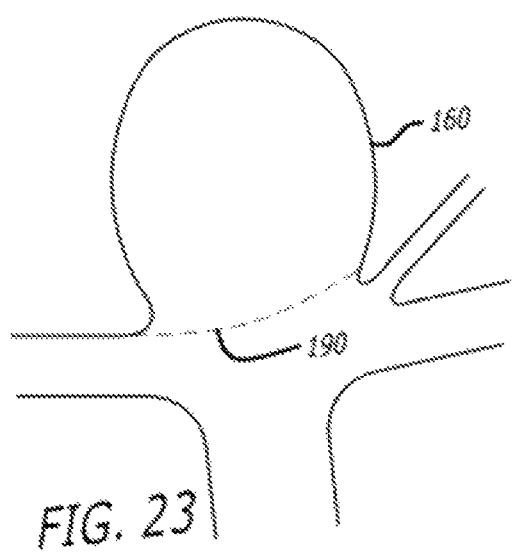
FIGS. 23-26 show a deployment sequence of a device for treatment of a patient's vasculature.
Figure 24:
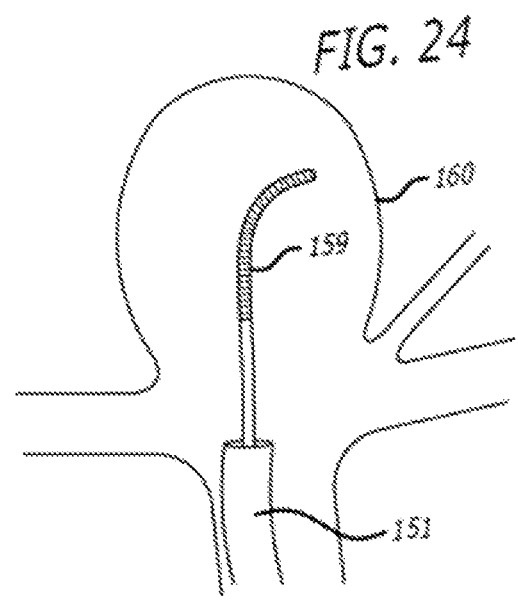

Once a properly sized device 10, 110 has been selected, the delivery and deployment process may then proceed. It should also be noted also that the properties of the device embodiments 10, 110 and delivery system embodiments 112 discussed herein generally allow for retraction of a device 10 after initial deployment into a defect 160, but before detachment of the device 10, 110. Therefore, it may also be possible and desirable to withdraw or retrieve an initially deployed device 10 after the fit within the defect 160 has been evaluated in favor of a differently sized device 10, 110. An example of a terminal aneurysm 160 is shown in FIG. 23 in section. The tip 151 of a catheter, such as a microcatheter 61 may be advanced into or adjacent the vascular site or defect 160 (e.g., aneurysm) as shown in FIG. 24. For some embodiments, an embolic coil or other vaso-occlusive device or material 176 (as shown for example in FIG. 19) may optionally be placed within the aneurysm 160 to provide a framework for receiving the device 10, 110. In addition, a stent 173 may be placed within a parent vessel 174 of some aneurysms substantially crossing the aneurysm neck prior to or during delivery of devices for treatment of a patient's vasculature discussed herein (also as shown for example in FIG. 19). An example of a suitable microcatheter 61 having an inner lumen diameter of about 0.020 inches to about 0.022 inches is the Rapid Transit® manufactured by Cordis Corporation. Examples of some suitable microcatheters 61 may include microcatheters having an inner lumen diameter of about 0.026 inch to about 0.028 inch, such as the Rebar® by Ev3 Company, the Renegade Hi-Flow® by Boston Scientific Corporation, and the Mass Transit® by Cordis Corporation. Suitable microcatheters having an inner lumen diameter of about 0.031 inch to about 0.033 inch may include the Marksmen® by Chestnut Medical Technologies, Inc. and the Vasco 28® by Balt Extrusion. A suitable microcatheter 61 having an inner lumen diameter of about 0.039 inch to about 0.041 inch includes the Vasco 35 by Balt Extrusion. These microcatheters 61 are listed as exemplary embodiments only, other suitable microcatheters may also be used with any of the embodiments discussed herein.

Figure 25:
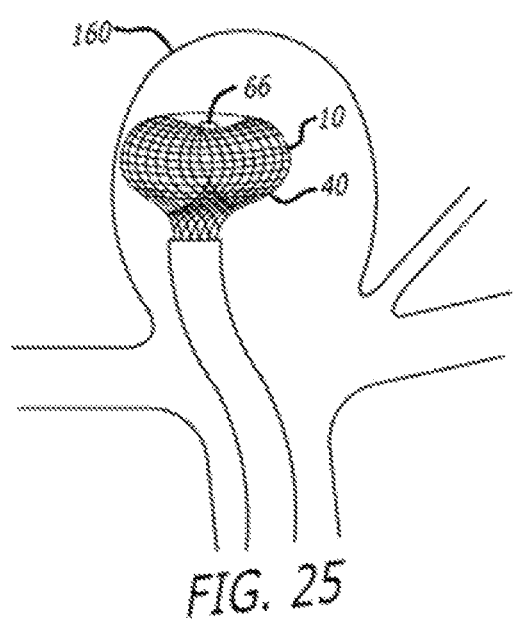

Detachment of the device 10, 110 from the delivery apparatus 111 may be controlled by a control switch 188 disposed at a proximal end of the delivery system 112, which may also be coupled to an energy source 142, which severs the tether 72 that secures the proximal hub 68 of the device 10 to the delivery apparatus 111. While disposed within the microcatheter 61 or other suitable delivery system 112, as shown in FIG. 11, the filaments 14, 114 of the permeable shell 40, 140 may take on an elongated, non-everted configuration substantially parallel to each other and a longitudinal axis of the catheter 61. Once the device 10, 110 is pushed out of the distal port of the microcatheter 61, or the radial constraint is otherwise removed, the distal ends 62 of the filaments 14, 114 may then axially contract towards each other so as to assume the globular everted configuration within the vascular defect 160 as shown in FIG. 25.

The device 10, 110 may be inserted through the microcatheter 61 such that the catheter lumen 120 restrains radial expansion of the device 10, 110 during delivery. Once the distal tip or deployment port of the delivery system 112 is positioned in a desirable location adjacent or within a vascular defect 160, the device 10, 110 may be deployed out the distal end of the catheter 61 thus allowing the device to begin to radially expand as shown in FIG. 25. As the device 10, 110 emerges from the distal end of the delivery system 112, the device 10, 110 expands to an expanded state within the vascular defect 160, but may be at least partially constrained by an interior surface of the vascular defect 160.

Figure 26:
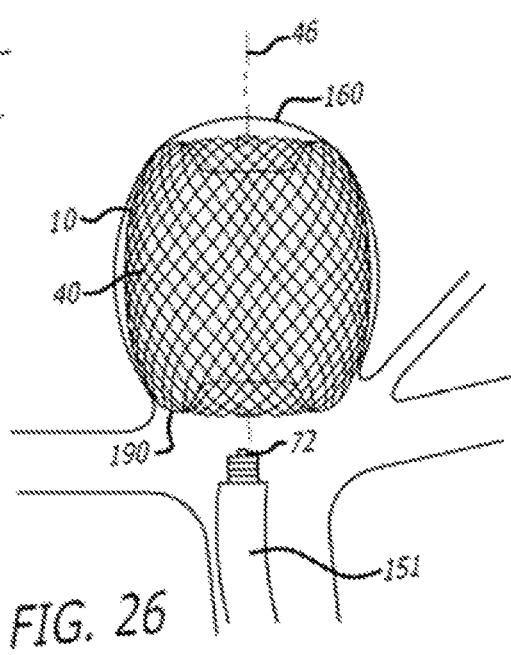

Upon full deployment, radial expansion of the device 10, 110 may serve to secure the device 10, 110 within the vascular defect 160 and also deploy the permeable shell 40 across at least a portion of an opening 190 (e.g., aneurysm neck) so as to at least partially isolate the vascular defect 160 from flow, pressure or both of the patient's vasculature adjacent the vascular defect 160 as shown in FIG. 26. The conformability of the device 10, 110, particularly in the neck region 190 may provide for improved sealing. For some embodiments, once deployed, the permeable shell 40, 140 may substantially slow the flow of fluids and impede flow into the vascular site and thus reduce pressure within the vascular defect 160. For some embodiments, the device 10, 110 may be implanted substantially within the vascular defect 160, however, in some embodiments, a portion of the device 10, 110 may extend into the defect opening or neck 190 or into branch vessels.

For some embodiments, as discussed above, the device 10, 110 may be manipulated by the user to position the device 10, 110 within the vascular site or defect 160 during or after deployment but prior to detachment. For some embodiments, the device 10, 110 may be rotated in order to achieve a desired position of the device 10 and, more specifically, a desired position of the permeable shell 40, 140, 240, 340, 440, prior to or during deployment of the device 10, 110. For some embodiments, the device 10, 110 may be rotated about a longitudinal axis of the delivery system 112 with or without the transmission or manifestation of torque being exhibited along a middle portion of a delivery catheter being used for the delivery. It may be desirable in some circumstances to determine whether acute occlusion of the vascular defect 160 has occurred prior to detachment of the device 10, 110 from the delivery apparatus 111 of the delivery system 112. These delivery and deployment methods may be used for deployment within berry aneurysms, terminal aneurysms, or any other suitable vascular defect embodiments 160. Some method embodiments include deploying the device 10, 110 at a confluence of three vessels of the patient's vasculature that form a bifurcation such that the permeable shell 40 of the device 10, 110 substantially covers the neck of a terminal aneurysm. Once the physician is satisfied with the deployment, size and position of the device 10, 110, the device 10, 110 may then be detached by actuation of the control switch 188 by the methods described above and shown in FIG. 26. Thereafter, the device 10, 110 is in an implanted state within the vascular defect 160 to effect treatment thereof.

Figure 27:
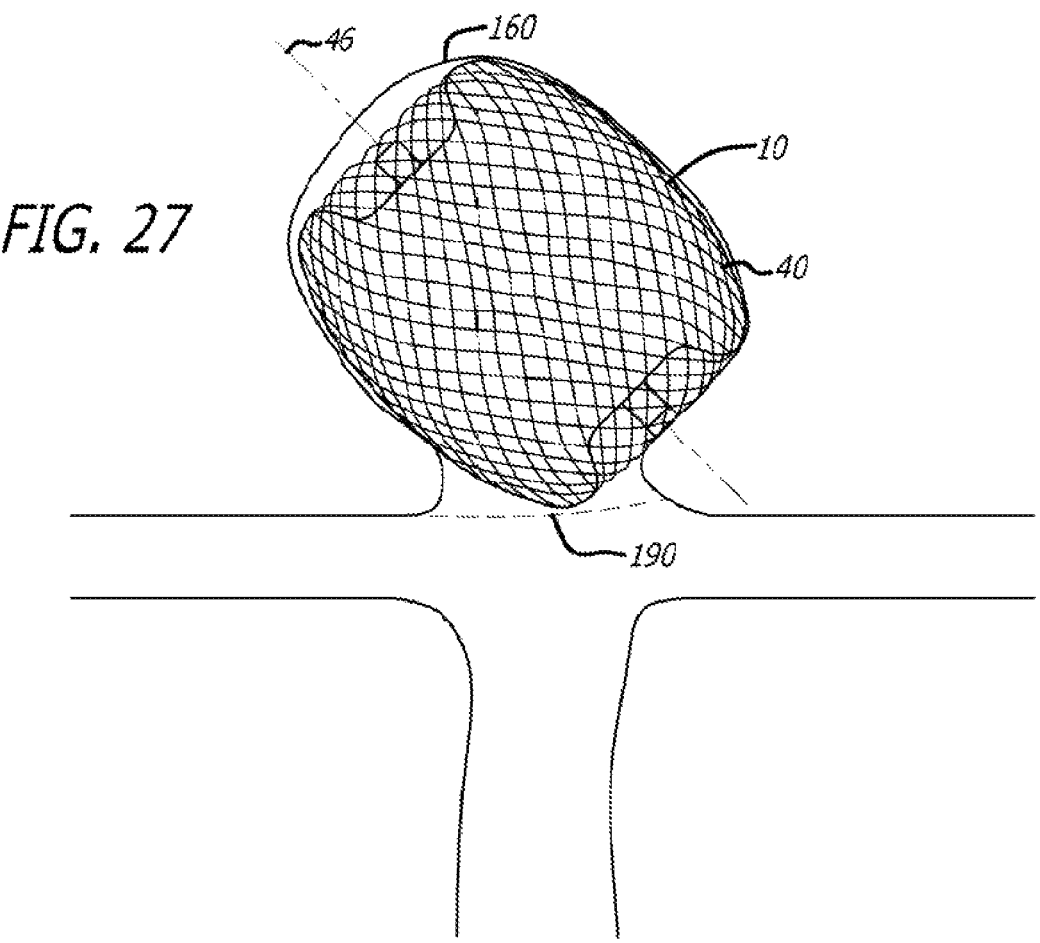
FIG. 27 is an elevation view in partial section of an embodiment of a device for treatment of a patient's vasculature deployed within an aneurysm at a tilted angle.

FIG. 27 illustrates another configuration of a deployed and implanted device in a patient's vascular defect 160. While the implantation configuration shown in FIG. 26 indicates a configuration whereby the longitudinal axis 46 of the device 10, 110 is substantially aligned with a longitudinal axis of the defect 160, other suitable and clinically effective implantation embodiments may be used. For example, FIG. 27 shows an implantation embodiment whereby the longitudinal axis 46 of the implanted device 10, 110 is canted at an angle of about 10 degrees to about 90 degrees relative to a longitudinal axis of the target vascular defect 160. Such an alternative implantation configuration may also be useful in achieving a desired clinical outcome with acute occlusion of the vascular defect 160 in some cases and restoration of normal blood flow adjacent the treated vascular defect. FIG. 28 illustrates a device 10, 110 implanted in an irregularly shaped vascular defect 160. The aneurysm 160 shown has at least two distinct lobes 192 extending from the main aneurysm cavity. The two lobes 192 shown are unfilled by the deployed vascular device 10, 110, yet the lobes 192 are still isolated from the parent vessel of the patient's body due to the occlusion of the aneurysm neck portion 190.

Markers, such as radiopaque markers, on the device 10, 110 or delivery system 112 may be used in conjunction with external imaging equipment (e.g., x-ray) to facilitate positioning of the device or delivery system during deployment. Once the device is properly positioned, the device 10 may be detached by the user. For some embodiments, the detachment of the device 10, 110 from the delivery apparatus 111 of the delivery system 112 may be affected by the delivery of energy (e.g., heat, radiofrequency, ultrasound, vibrational, or laser) to a junction or release mechanism between the device 10 and the delivery apparatus 111. Once the device 10, 110 has been detached, the delivery system 112 may be withdrawn from the patient's vasculature or patient's body 158. For some embodiments, a stent 173 may be place within the parent vessel substantially crossing the aneurysm neck 190 after delivery of the device 10 as shown in FIG. 19 for illustration.

For some embodiments, a biologically active agent or a passive therapeutic agent may be released from a responsive material component of the device 10, 110. The agent release may be affected by one or more of the body's environmental parameters or energy may be delivered (from an internal or external source) to the device 10, 110. Hemostasis may occur within the vascular defect 160 as a result of the isolation of the vascular defect 160, ultimately leading to clotting and substantial occlusion of the vascular defect 160 by a combination of thrombotic material and the device 10, 110. For some embodiments, thrombosis within the vascular defect 160 may be facilitated by agents released from the device 10 and/or drugs or other therapeutic agents delivered to the patient.

For some embodiments, once the device 10, 110 has been deployed, the attachment of platelets to the permeable shell 40 may be inhibited and the formation of clot within an interior space of the vascular defect 160, device, or both promoted or otherwise facilitated with a suitable choice of thrombogenic coatings, anti-thrombogenic coatings or any other suitable coatings (not shown) which may be disposed on any portion of the device 10, 110 for some embodiments, including an outer surface of the filaments 14 or the hubs 66 and 68. Such a coating or coatings may be applied to any suitable portion of the permeable shell 40. Energy forms may also be applied through the delivery apparatus 111 and/or a separate catheter to facilitate fixation and/or healing of the device 10, 110 adjacent the vascular defect 160 for some embodiments. One or more embolic devices or embolic material 176 may also optionally be delivered into the vascular defect 160 adjacent permeable shell portion that spans the neck or opening 190 of the vascular defect 160 after the device 10 has been deployed. For some embodiments, a stent or stent-like support device 173 may be implanted or deployed in a parent vessel adjacent the defect 160 such that it spans across the vascular defect 160 prior to or after deployment of the vascular defect treatment device 10, 110.

In any of the above embodiments, the device 10, 110 may have sufficient radial compliance so as to be readily retrievable or retractable into a typical microcatheter 61. The proximal portion of the device 10, 110, or the device as a whole for some embodiments, may be engineered or modified by the use of reduced diameter filaments, tapered filaments, or filaments oriented for radial flexure so that the device 10, 110 is retractable into a tube that has an internal diameter that is less than about 0.7 mm, using a retraction force less than about 2.7 Newtons (0.6 lbf) force. The force for retrieving the device 10, 110 into a microcatheter 61 may be between about 0.8 Newtons (0.18 lbf) and about 2.25 Newtons (0.5 lbf).

Figure 29:
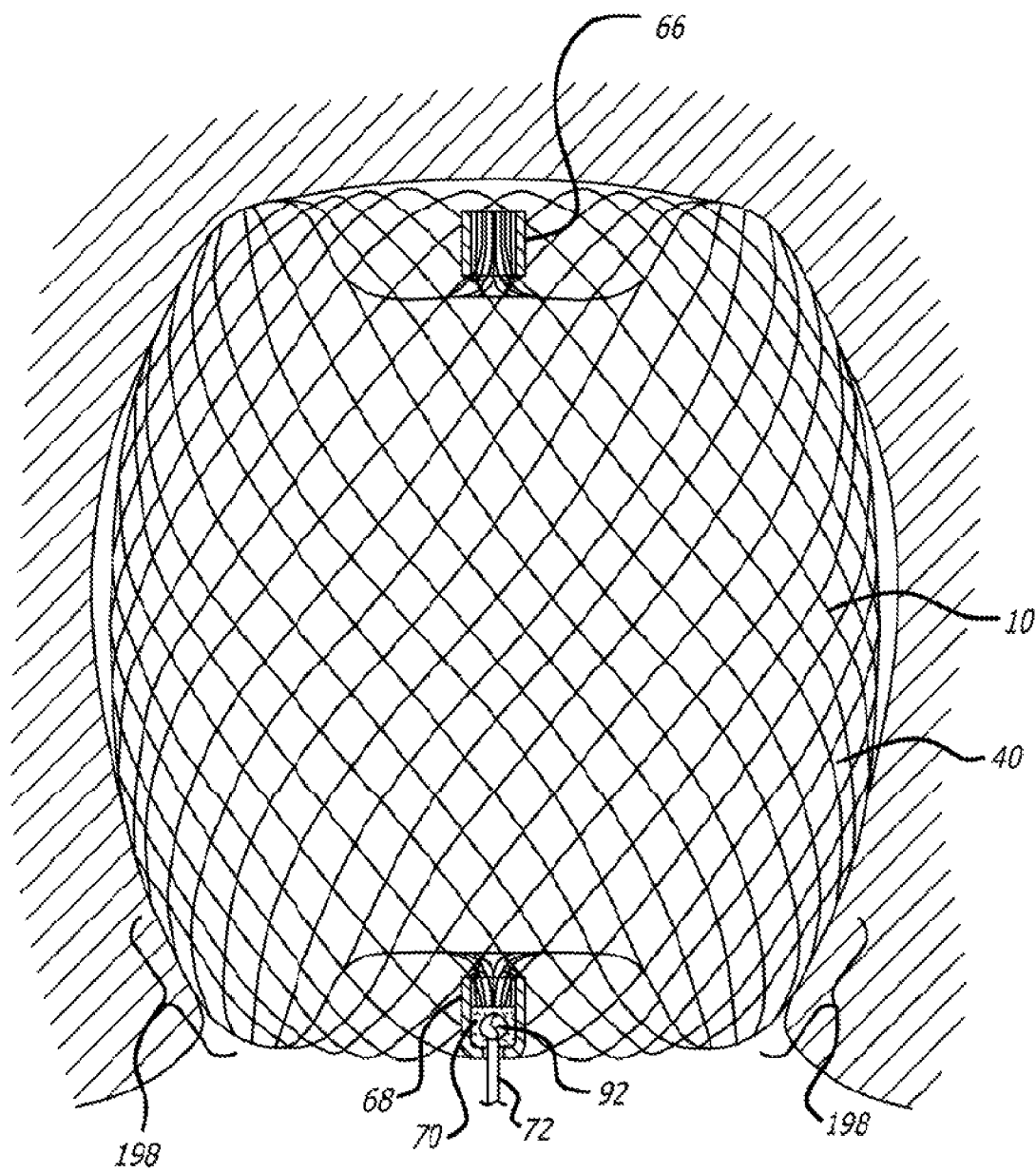
FIG. 29 shows an elevation view in section of a device for treatment of a patient's vasculature deployed within a vascular defect aneurysm.

Engagement of the permeable shell 40, 140 with tissue of an inner surface of a vascular defect 160, when in an expanded relaxed state, may be achieved by the exertion of an outward radial force against tissue of the inside surface of the cavity of the patient's vascular defect 160, as shown for example in FIG. 29. A similar outward radial force may also be applied by a proximal end portion and permeable shell 40, 140 of the device 10, 110 so as to engage the permeable shell 40 with an inside surface or adjacent tissue of the vascular defect 160. Such forces may be exerted in some embodiments wherein the nominal outer transverse dimension or diameter of the permeable shell 40 in the relaxed unconstrained state is larger than the nominal inner transverse dimension of the vascular defect 160 within which the device 10, 110 is being deployed, i.e., oversizing as discussed above. The elastic resiliency of the permeable shell 40 and filaments 14 thereof may be achieved by an appropriate selection of materials, such as superelastic alloys, including nickel titanium alloys, or any other suitable material for some embodiments. The conformability of a proximal portion of the permeable shell 40, 140 of the device 10, 110 may be such that it will readily ovalize to adapt to the shape and size of an aneurysm neck 190, as shown in FIGS. 20-22, thus providing a good seal and barrier to flow around the device. Thus, the device 10 may achieve a good seal, substantially preventing flow around the device without the need for fixation members that protrude into the parent vessel.

Various aspects of the present subject matter are set forth below, in review of, and/or in supplementation to, the embodiments described thus far, with the emphasis here being on the interrelation and interchangeability of the following embodiments. In other words, an emphasis is on the fact that each feature of the embodiments can be combined with each and every other feature unless explicitly stated otherwise or logically implausible. The embodiments described herein are restated and expanded upon in the following paragraphs without explicit reference to the figures.

In many embodiments, a device for treatment of a patient's cerebral aneurysm includes: a plurality of permeable shells, each having a proximal end, a distal end, a radially constrained elongated state configured for delivery within a catheter lumen, an expanded state with a longitudinally shortened configuration relative to the radially constrained state, and a plurality of elongate filaments that are woven together to form a mesh; and a plurality of coils, wherein each coil of the plurality of coils connects at least one pair of permeable shells in the plurality of permeable shells.

In some embodiments, the plurality of permeable shells are in a substantially linear arrangement.

In some embodiments, the expanded states of each of the permeable shells of the plurality of permeable shells have a different diameter.

In some embodiments, the expanded states of each of the permeable shells of the plurality of permeable shells have the same diameter.

In some embodiments, the expanded state of a distal most permeable shell has a smaller diameter than the diameter of the expanded state of a proximal most permeable shell.

In some embodiments, the expanded states of each permeable shell of the plurality of permeable shells has a diameter between about 2 mm and about 10 mm.

In some embodiments, the plurality of permeable shells includes between about five and about nine permeable shells.

In some embodiments, each coil of the plurality of coils has an internal diameter between about 2 mm and about 8 mm.

In some embodiments, each coil of the plurality of coils comprises an inert hydrogel core that absorbs water.

In some embodiments, the device has an overall shape that is a helix.

In some embodiments, a total length of the device is less than about 100 cm.

In some embodiments, the device has a proximal end and a distal end, and wherein a coil connecting a pair of permeable shells near the proximal end has a larger diameter than a coil connecting a pair of permeable shells near the distal end.

In many embodiments, a method for treating a cerebral aneurysm having an interior cavity and a neck includes the steps of: advancing an implant in a microcatheter to a region of interest in a cerebral artery, wherein the implant comprises: a plurality of permeable shells, each having a proximal end, a distal end, a radially constrained elongated state configured for delivery within a catheter lumen, an expanded state with a longitudinally shortened configuration relative to the radially constrained state, and a plurality of elongate filaments that are woven together to form a mesh, wherein the plurality of permeable shells includes at least one pair of permeable shells; and a plurality of coils, wherein each coil of the plurality of coils connects at least one pair of permeable shells in the plurality of permeable shells; deploying the implant within the cerebral aneurysm, wherein each of the permeable shells of the plurality of permeable shells expands to its expanded state in the interior cavity of the aneurysm; and withdrawing the microcatheter from the region of interest after deploying the implant.

In some embodiments, the plurality of permeable shells are in a substantially linear arrangement.

In some embodiments, the expanded states of each of the permeable shells of the plurality of permeable shells have a different diameter.

In some embodiments, the expanded states of each of the permeable shells of the plurality of permeable shells have the same diameter.

In some embodiments, the expanded state of a distal most permeable shell has a smaller diameter than the diameter of the expanded state of a proximal most permeable shell.

In some embodiments, the expanded states of each permeable shell of the plurality of permeable shells has a diameter between about 2 mm and about 10 mm.

In some embodiments, the plurality of permeable shells includes between about five and about nine permeable shells.

In some embodiments, each coil of the plurality of coils has an internal diameter between about 2 mm and about 8 mm.

In some embodiments, each coil of the plurality of coils comprises an inert hydrogel core that absorbs water.

In some embodiments, the device has an overall shape that is a helix.

In some embodiments, a total length of the device is implant than about 100 cm.

In some embodiments, the implant has a proximal end and a distal end, and wherein a coil connecting a pair of permeable shells near the proximal end has a larger diameter than a coil connecting a pair of permeable shells near the distal end.

In many embodiments, a device for treatment of a patient's cerebral aneurysm includes: a first permeable shell having a proximal end, a distal end, a radially constrained elongated state configured for delivery within a catheter lumen, an expanded state with a longitudinally shortened configuration relative to the radially constrained state, and a plurality of elongate filaments that are woven together to form a mesh; a second permeable shell having a proximal end, a distal end, a radially constrained elongated state configured for delivery within a catheter lumen, an expanded state with a longitudinally shortened configuration relative to the radially constrained state, and a plurality of elongate filaments that are woven together to form a mesh;

and a first coil coupling the proximal end of the first permeable shell to the distal end of the second permeable shell.

In some embodiments, the device further includes a third permeable shell having a proximal end, a distal end, a radially constrained elongated state configured for delivery within a catheter lumen, an expanded state with a longitudinally shortened configuration relative to the radially constrained state, and a plurality of elongate filaments that are woven together to form a mesh; and a second coil coupling the proximal end of the second permeable shell to the distal end of the third permeable shell.

In some embodiments, the device further includes at least an additional permeable shell having a proximal end, a distal end, a radially constrained elongated state configured for delivery within a catheter lumen, an expanded state with a longitudinally shortened configuration relative to the radially constrained state, and a plurality of elongate filaments that are woven together to form a mesh; and at least an additional coil coupling the proximal end of the third permeable shell to the distal end of the at least an additional permeable shell.

In some embodiments, the first coil comprises an inert hydrogel core that absorbs water.

In some embodiments, the expanded state of the first permeable shell and the expanded state of the second permeable shell have the same diameters.

In some embodiments, the expanded state of the first permeable shell and the expanded state of the second permeable shell have the different diameters.

In some embodiments, a total length of the device is less than about 100 cm.

In some embodiments, the device has a proximal end and a distal end, and wherein a coil connecting a pair of permeable shells near the proximal end has a larger diameter than a coil connecting a pair of permeable shells near the distal end.

Although the foregoing invention has, for the purposes of clarity and understanding, been described in some detail by way of illustration and example, it will be obvious that certain changes and modifications may be practiced which will still fall within the scope of the appended claims. All applications, publications, and references mentioned in this application are expressly incorporated by reference in their entirety for all purposes.

What is claimed is:

1. A device for treatment of a patient's cerebral aneurysm, comprising:
   a plurality of permeable shells comprising at least a first permeable shell and a second permeable shell, each permeable shell of the plurality of permeable shells having a proximal end, a distal end, a plurality of elongate filaments that are woven together to form a mesh, a radially constrained elongated state configured for delivery within a catheter lumen, and an expanded state with a longitudinally shortened configuration relative to the radially constrained state, the expanded state comprising a hollow inner cavity, wherein each of the plurality of elongate filaments has a proximal end and a distal end, wherein the proximal ends of each of the plurality of elongate filaments are gathered in a proximal hub and the distal ends of each of the plurality of elongate filaments are gathered in a distal hub; and
   a plurality of coils, wherein each coil of the plurality of coils comprises an inert hydrogel core that absorbs water, and wherein a first coil of the plurality of coils connects a proximal hub of the first permeable shell and a distal hub of the second permeable shell.

2. The system of claim 1, wherein the plurality of permeable shells are in a substantially linear arrangement.

3. The system of claim 1, wherein the expanded states of each of the permeable shells of the plurality of permeable shells have a different diameter.

4. The system of claim 1, wherein the expanded states of each of the permeable shells of the plurality of permeable shells have the same diameter.

5. The system of claim 1, wherein the expanded state of a distal most permeable shell has a smaller diameter than the diameter of the expanded state of a proximal most permeable shell.

6. The system of claim 1, wherein the expanded states of each permeable shell of the plurality of permeable shells has a diameter between about 2 mm and about 10 mm.

7. The system of claim 1, wherein the plurality of permeable shells includes between about five and about nine permeable shells.

8. The system of claim 1, wherein each coil of the plurality of coils has an internal diameter between about 2 mm and about 8 mm.

9. The system of claim 1, wherein the device has an overall shape that is a helix.

10. The system of claim 1, wherein a total length of the device is less than about 100 cm.

11. The system of claim 1, wherein the device has a proximal end and a distal end, and wherein a coil connecting a pair of permeable shells near the proximal end has a larger diameter than a coil connecting a pair of permeable shells near the distal end.

12. The system of claim 1, further comprising an embolic material configured for delivery into the patient's cerebral aneurysm.

13. A system for treatment of a patient's cerebral aneurysm, comprising:
   a first permeable shell having a proximal end, a distal end, a radially constrained elongated state configured for delivery within a catheter lumen, an expanded state with a longitudinally shortened configuration relative to the radially constrained state, the expanded state of the first permeable shell comprising a first hollow inner cavity, and a first plurality of elongate filaments that are woven together to form a mesh, wherein each of the first plurality of elongate filaments has a proximal end and a distal end, wherein the proximal ends of each of the first plurality of elongate filaments are gathered at the proximal end of the first permeable shell and wherein the distal ends of each of the first plurality of elongate filaments are gathered at the distal end of the first permeable shell;
   a second permeable shell having a proximal end, a distal end, a radially constrained elongated state configured for delivery within the catheter lumen, an expanded state with a longitudinally shortened configuration relative to the radially constrained state of the second permeable shell, the expanded state of the second permeable shell comprising a second hollow inner cavity, and a second plurality of elongate filaments that are woven together to form a mesh, wherein each of the second plurality of elongate filaments has a proximal end and a distal end, wherein the proximal ends of each of the second plurality of elongate filaments are gathered at the proximal end of the second permeable shell and wherein the distal ends of each of the second plurality of elongate filaments are gathered at the distal end of the second permeable shell, wherein the first plurality of elongate filaments is different than the second plurality of elongate filaments; and a first coil coupling the proximal end of the first permeable shell to the distal end of the second permeable shell, wherein the first coil comprises an inert hydrogel core that absorbs water, and wherein the first hollow inner cavity and the second hollow inner cavity each do not contain a portion of the first coil.

14. The system of claim 13, wherein the device further comprises a third permeable shell having a proximal end, a distal end, a radially constrained elongated state configured for delivery within the catheter lumen, an expanded state with a longitudinally shortened configuration relative to the radially constrained state of the third permeable shell, the expanded state of the third permeable shell comprising a hollow inner cavity, and a plurality of elongate filaments that are woven together to form a mesh; and a second coil coupling the proximal end of the second permeable shell to the distal end of the third permeable shell.

15. The system of claim 14, further comprising at least one additional permeable shell having a proximal end, a distal end, a radially constrained elongated state configured for delivery within the catheter lumen, an expanded state with a longitudinally shortened configuration relative to the radially constrained state the at least one additional, the expanded state of the at least one permeable shell comprising a hollow inner cavity, and a plurality of elongate filaments that are woven together to form a mesh; and at least one additional coil coupling the proximal end of the third permeable shell to the distal end of the at least one additional permeable shell.

16. The system of claim 13, wherein the first coil has a diameter that is greater than a diameter of the second coil.

17. The system of claim 13, wherein the expanded state of the first permeable shell and the expanded state of the second permeable shell have the same diameters.

18. The system of claim 13, wherein the expanded state of the first permeable shell and the expanded state of the second permeable shell have different diameters.

19. The system of claim 13, wherein a total length of the device is less than about 100 cm.

20. The system of claim 13, further comprising an embolic material configured for delivery into the patient's cerebral aneurysm.

21. A system for treatment of a patient's cerebral aneurysm, comprising:

a first permeable shell having a proximal end, a distal end, a radially constrained elongated state configured for delivery within a catheter lumen, an expanded state with a longitudinally shortened configuration relative to the radially constrained state, the expanded state of the first permeable shell comprising a first hollow inner cavity, and a first plurality of elongate filaments that are woven together to form a mesh, wherein each of the first plurality of elongate filaments has a proximal end and a distal end, wherein the proximal ends of each of the first plurality of elongate filaments are gathered at the proximal end of the first permeable shell in a first proximal hub and wherein the distal ends of each of the first plurality of elongate filaments are gathered at the distal end of the first permeable shell in a first distal hub;

a second permeable shell having a proximal end, a distal end, a radially constrained elongated state configured for delivery within the catheter lumen, an expanded state with a longitudinally shortened configuration relative to the radially constrained state of the second permeable shell, the expanded state of the second permeable shell comprising a second hollow inner cavity, and a second plurality of elongate filaments that are woven together to form a mesh, wherein each of the second plurality of elongate filaments has a proximal end and a distal end, wherein the proximal ends of each of the second plurality of elongate filaments are gathered at the proximal end of the second permeable shell in a second proximal hub and wherein the distal ends of each of the second plurality of elongate filaments are gathered at the distal end of the second permeable shell in a second distal hub, wherein the first plurality of elongate filaments is different than the second plurality of elongate filaments; and a first coil coupling the first proximal hub to the second distal hub, wherein the first coil comprises an inert hydrogel core that absorbs water.

22. The system of claim 21, further comprising an embolic material configured for delivery into the patient's cerebral aneurysm.

* * * * *